(12) United States Patent
Young et al.

(10) Patent No.: US 7,763,634 B2
(45) Date of Patent: Jul. 27, 2010

(54) INHIBITORS OF JANUS KINASES

(75) Inventors: Jonathan R. Young, Southborough, MA (US); Andrew Haidle, Cambridge, MA (US); Paul Tempest, Brookline, MA (US); Michelle Machacek, Boston, MA (US)

(73) Assignees: Merck & Co., Inc., Rahway, NJ (US); Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 12/227,959

(22) PCT Filed: Jun. 5, 2007

(86) PCT No.: PCT/US2007/013255

§ 371 (c)(1),
(2), (4) Date: Dec. 3, 2008

(87) PCT Pub. No.: WO2007/145957

PCT Pub. Date: Dec. 21, 2007

(65) Prior Publication Data

US 2009/0306071 A1 Dec. 10, 2009

Related U.S. Application Data

(60) Provisional application No. 60/812,524, filed on Jun. 9, 2006.

(51) Int. Cl.
*A61K 31/4745* (2006.01)
*C07D 471/02* (2006.01)

(52) U.S. Cl. .................. 514/287; 546/64; 544/125; 544/242; 544/361; 514/232.8; 514/253; 514/256

(58) Field of Classification Search ............... 514/287, 514/232.8, 253, 256; 546/64; 544/125, 242, 544/361

See application file for complete search history.

(56) References Cited

U.S. PATENT DOCUMENTS 6,852,727 B2 * 2/2005 Goulet et al. ............... 514/287
2006/0106020 A1 5/2006 Rodgers et al.

FOREIGN PATENT DOCUMENTS

WO    WO 03/011285    2/2003
WO    WO 2005/105814    11/2005

OTHER PUBLICATIONS

Lucet, IS et al., Blood, vol. 207, No. 1, pp. 176-183 (2006), "The structural basis of Janus kinase 2 inhibition by a potent and specific pan-Janus kinase inhibitor".
Thompson, JE et al., Biorganic & Medicinal Chemistry Letters, vol. 12, pp. 1219-1223 (2002), "Photochemical preparation of a pyridone containing tetracycle: A Jak protein kinase inhibitor".
Pfizer Products, Expert Opinion on Therapeutic Patents, vol. 13, No. 7, pp. 1087-1092 (2003), "Pyrrolo[2,3[pyrimidine inhibitors of Janus kinase 2 protein tyrosine kinase".

* cited by examiner

*Primary Examiner*—Charanjit S Aulakh
(74) *Attorney, Agent, or Firm*—Nicole M. Beeler; David A. Muthard

(57) ABSTRACT

The instant invention provides for tetracyclic compounds that inhibit the four known mammalian JAK kinases (JAK1, JAK2, JAK3 and TYK2) and PDK1. The invention also provides for compositions comprising such inhibitory compounds and methods of inhibiting the activity of JAK1, JAK2, JAK3 TYK2 and PDK1 by administering the compound to a patient in need of treatment for myeloproliferative disorders or cancer.

7 Claims, No Drawings ial antigens usually involving CD4+ T helper cells (TH2) which are triggered from cytokines IL-4, IL-5, IL-6, IL-10, and IL-13 which signal through JAK1/JAK3-STAT6 pathway. Th1 cells are thought to be involved with the "delayed-type hypersensitivity responses" which secrete IL-2, IFN-γ, and TNF-β and signal through the JAK2/TYK2-STAT4 pathway. STAT6 (−/−) mice were protected from AHR when challenged with environmental antigens and showed no increase in IgE levels or the quantity of mucous containing cells.

SEQUENCE LISTING

```
<160> NUMBER OF SEQ ID NOS: 2

<210> SEQ ID NO 1
<211> LENGTH: 15
<212> TYPE: PRT
<213> ORGANISM: Artificial Sequence
<220> FEATURE:
<223> OTHER INFORMATION: Completely synthetic
<220> FEATURE:
<221> NAME/KEY: AMIDATION
<222> LOCATION: (15)...(15)

<400> SEQUENCE: 1

Glu Gln Glu Asp Glu Pro Glu Gly Asp Tyr Phe Glu Trp Leu Glu
1               5                   10                  15

<210> SEQ ID NO 2
<211> LENGTH: 28
<212> TYPE: PRT
<213> ORGANISM: Artificial Sequence
<220> FEATURE:
<223> OTHER INFORMATION: Completely synthetic

<400> SEQUENCE: 2

Gly Gly Asp Gly Ala Thr Met Lys Thr Phe Cys Gly Gly Thr Pro Ser
1               5                   10                  15

Asp Gly Asp Pro Asp Gly Gly Glu Phe Thr Glu Phe
                20                  25
```

INHIBITORS OF JANUS KINASES

PRIORITY CLAIM

This application is a §371 National Stage Application of PCT/US2007/013255 filed on Jun. 5, 2007, which claims priority from U.S. Provisional Application Ser. No. 60/812,524, filed on Jun. 9, 2006.

BACKGROUND OF THE INVENTION

Janus kinase (JAK) is a family of intracellular non-receptor tyrosine kinases, ranging from 120-140 kDa, that transduce cytokine-mediated signals via the JAK-STAT pathway. The JAK family plays a role in the cytokine-dependent regulation of proliferation and function of cells involved in immune response. Currently, there are four known mammalian JAK family members: JAK1, JAK2, JAK3 and TYK2.

JAK1, JAK2 and TYK2 are ubiquitously expressed whereas JAK3 is expressed in the myeloid and lymphoid lineages. The JAK family members are non-receptor tyrosine kinases that associate with many hematopoietin cytokines, receptor tyrosine kinases and GPCR's. JAK1−/− mice were found to be developmentally similar to the JAK1+/+ although they weighed 40% less than the wild-type and failed to nurse at birth. These pups were not viable and died within 24 hours of birth (Meraz et al Cell, 1998, 373-383). JAK1 deficiency led to reduced number of thymocytes, pre-B cells and mature T and B lymphocytes. TYK2(−/−) mice, on the other hand, are viable, demonstrating subtle defects in their response to IFN-α/β and IL-10 and profound defects to the response of IL-12 and LPS.

The breast cancer susceptibility protein (BRCA1) acts as a tumor suppressor and contributes to cell proliferation, cycle regulation, as well as DNA damage and repair. BRCA1 (−/−) mice develop normally but die by 7.5 days post embryo suggesting a key role of BRCA1 for development. Mice in which the BRCA1 protein was overexpressed led to inhibition of cell growth and sensitized cells to cytotoxic reagents. In the human prostate cancer cell line Du-145(Gao FEBS Letters 2001, 488, 179-184), enhanced expression of BRCA1 was found to correlate with constitutive activation of STAT3 as well as activation of JAK1 and JAK2. Moreover, antisense oligonucleotides selective for STAT3 led to significant inhibition of cell proliferation and apoptosis in Du-145 cells. This data supports the potential utility of JAK1 and JAK2inhibitors in the treatment of prostate cancer.

Campbell et al (Journal of Biological Chemistry 1997, 272, 2591-2594) as reported that STAT3 is constitutively activated v-Src transformed cells. To test whether STAT3activation resulted via signaling through the JAK-STAT pathway, three fibroblast cell lines (NIH3T3, Balb/c, and 3Y1) were transformed with v-Src. The level of JAK1 phosphorylation in NIH3T3 cells was markedly increased in cells overexpressed with v-Src or mutant c-Src (Y527F) compared to those in the less transforming c-Src. This result correlated with increased JAK1 enzymatic activity. Similar results were observed with JAK2 albeit to a lesser extent. These results are consistent with constitutive activation of JAK1 and possibly JAK2 which contribute to the hyperactivation of STAT3 in Src-transformed cells.

Asthma is a disease that is increasing in prevalence and results in "airway obstruction, airway hyperresponsiveness, and airway inflammation and remodeling" (Pernis The Journal of Clinical Investigation 2002, 109, 1279-1283). A common cause is the inappropriate immune responses to environmental antigens usually involving CD4+ T helper cells (TH2)

JAK2 is a cytoplasmic protein-tyrosine kinase that catalyzes the transfer of the gamma-phosphate group of adenosine triphosphate to the hydroxyl groups of specific tyrosine residues in signal transduction molecules. JAK2 mediates signaling downstream of cytokine receptors after ligand-induced autophosphorylation of both receptor and enzyme. The main downstream effectors of JAK2 are a family of transcription factors known as signal transducers and activators of transcription (STAT) proteins. Studies have disclosed an association between an activating JAK2 mutation (JAK2V617F) and myleoproliferative disorders. The myeloproliferative disorders, a subgroup of myeloid malignancies, are clonal stem cell diseases characterized by an expansion of morphologically mature granulocyte, erythroid, megakaryocyte, or monocyte lineage cells. Myeloproliferative disorders (MPD) include polycythemia vera (PV), essential thrombocythemia (ET), myeloid metaplasia with myelofibrosis (MMM), chronic myelogenous leukemia (CML), chronic myelomonocytic leukemia (CMML), hypereosinophilic syndrome (HES), juvenile myelomonocytic leukemia (JMML) and systemic mast cell disease (SMCD). It has been suggested that abnormalties in signal transduction mechanisms, including constitutive activation of protein tyrosine kinases, initiate MPD.

JAK3 associates with the common gamma chain of the extracellular receptors for the following interleukins: IL-2, IL-4, IL-7, IL-9 and IL-15. A JAK3 deficiency is associated with an immune compromised (SCID) phenotype in both rodents and humans. The SCID phenotype of JAK3 −/− mammals and the lymphoid cell specific expression of JAK3 are two favorable attributes of a target for an immune suppressant. Data suggests that inhibitors of JAK3could impede T-cell activation and prevent rejection of grafts following transplant surgery, or to provide therapeutic benefit to patients suffering autoimmune disorders.

PDK1 signalling regulates multiple critical steps in angiogenesis. Inhibitors of the activity of PDK1 are thus useful in the treatment of cancer, in particular cancers associated with deregulated activity of the PTEN/P13K pathway including, but not limited to PTEN loss of function mutations and receptor tyrosine kinase gain of function mutations.

SUMMARY OF THE INVENTION

The instant invention provides for compounds that inhibit the four known mammalian JAK kinases (JAK1, JAK2, JAK3 and TYK2) and PDK1. The invention also provides for compositions comprising such inhibitory compounds and methods of inhibiting the activity of JAK1, JAK2, JAK3 TYK2 and PDK1 by administering the compound to a patient in need of treatment for myeloproliferative disorders or cancer. One embodiment of the invention is illustrated by a compound of the following formula, and the pharmaceutically acceptable salts and stereoisomers thereof:

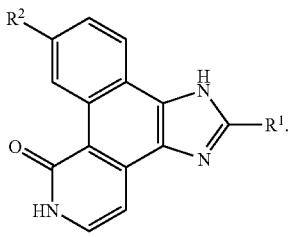

DETAILED DESCRIPTION OF THE INVENTION

The instant invention provides for compounds that inhibit the four known mammalian JAK kinases (JAK1, JAK2, JAK3 and TYK2) and PDK1. The invention also provides for compositions comprising such inhibitory compounds and methods of inhibiting the activity of JAK1, JAK2, JAK3, TYK2 and PDK1 by administering the compound to a patient in need of treatment for myeloproliferative disorders or cancer. One embodiment of the invention is illustrated by a compound of the formula

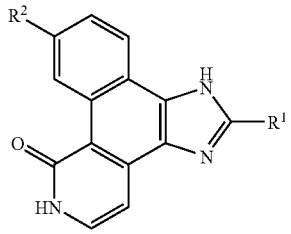

wherein $R^1$ is aryl, heteroaryl, heterocyclyl, $C_{3-8}$ cycloalkyl, or $C_{1-6}$ alkyl, wherein said aryl, heteroaryl, heterocyclyl, cycloalkyl and alkyl groups are optionally substituted with one to three substituents independently selected from the group consisting of halo, hydroxyl, $C_{1-6}$alkyl, $O(C_{1-6}$alkyl), $R^3$ and haloalkyl;

$R^2$ is aryl, heteroaryl, heterocyclyl, $C_{3-8}$ cycloalkyl, halo, $C_{1-6}$alkyl, (C=O)$R^3$, (C=O)NR$^4$(C$_{1-6}$alkyl)R$^3$, (C=O) NR$^4$SO$_m$C$_{1-6}$alkyl, (C=O)NR$^4$(C$_{1-6}$alkyl)NR$^4$R$^5$, NR$^4$- (C$_{1-6}$alkyl)-R$^3$, NR$^4$(C$_{1-6}$alkyl)OR$^5$, NR$^4$(C$_{1-6}$alkyl) NR$^4$R$^3$, NR$^4$R$^5$, NR$^4$R$^3$ or NR$^4$SO$_m$NR$^4$R$^5$, wherein said aryl, heteroaryl, heterocyclyl, cycloalkyl and alkyl groups are optionally substituted with one to three substituents independently selected from the group consisting of $R^3$, hydroxyl, cyano, halo, $C_{1-6}$alkyl, O(C$_{1-6}$alkyl), O(C$_{1-6}$ alkyl)R$^3$, (C$_{1-6}$alkyl)R$^3$, (C=O)R$^3$, OR$^3$, (C=O)R$^3$H, (C=O) R$^3$O(C$_{1-6}$alkyl), (C=O)O(C$_{1-6}$alkyl), R$^3$(C=O) O(C$_{1-6}$alkyl), SO$_m$R$^3$, SO$_m$R$^4$, (C=O)NR$^4$R$^5$, (C=O) NR$^4$(C$_{1-6}$alkyl)R$^3$; (C=O)NR$^4$(C$_{1-6}$alkyl)NR$^4$R$^5$, (C=O)O(C$_{1-6}$alkyl), (C=O)NR$^4$SO$_m$(C$_{1-6}$alkyl), NR$^4$R$^5$, (C=O)NR$^4$R$^5$, N(R$^3$)$_2$, NR$^4$(C$_{1-6}$alkyl)R$^3$, NR$^4$ (C=O)C$_{1-6}$alkyl, NR$^4$SO$_m$(C$_{1-6}$alkyl), (C$_{1-6}$alkyl)NR$^4$R$^5$ and NHSO$_m$ N(R$^3$)$_2$;

each $R^3$ is independently aryl, heteroaryl, heterocyclyl or $C_{3-8}$ cycloalkyl, wherein said aryl, heteroaryl, heterocyclyl and cycloalkyl groups are optionally substituted with one to three halo, hydroxyl or $C_{1-6}$ alkyl;

$R^4$ is hydrogen or $C_{1-6}$ alkyl;

$R^5$ is hydrogen or $C_{1-6}$ alkyl;

m is an integer from zero to two;

or a pharmaceutically acceptable salt or a stereoisomer thereof.

In an embodiment of the invention, $R^1$ is aryl or heteroaryl, wherein said aryl and heteroaryl groups are optionally substituted with one to three halo. In a class of the embodiment, $R^1$ is phenyl or pyridyl, wherein said phenyl and pyridyl groups are optionally substituted with one to three halo. In a subclass of the embodiment, $R^1$ is phenyl substituted with two halo.

In an embodiment of the invention, $R^2$ is heteroaryl, heterocyclyl, NR$^4$(C$_{1-6}$alkyl)R$^3$, NR$^4$(C$_{1-6}$alkyl)OR$^5$, NR$^4$(C$_{1-6}$ alkyl)NR$^3$, NR$^4$R$^5$ or NR$^4$SO$_m$NR$^4$R$^5$, wherein said heteroaryl, heterocyclyl and alkyl groups are optionally substituted with one to three substituents independently selected from the group consisting of $R^3$, hydroxyl, cyano and halo. In a class of the embodiment, $R^2$ is heteroaryl, NR$^4$(C$_{1-6}$alkyl) R$^3$, NR$^4$(C$_{1-6}$alkyl)OR$^5$ or NR$^4$R$^5$ wherein said heteroaryl and alkyl groups are optionally substituted with one to three substituents independently selected from the group consisting of hydroxyl, cyano and halo. In a subclass of the embodiment, $R^2$ is heteroaryl wherein said heteroaryl and alkyl group is optionally substituted with one to two substituents independently selected from the group consisting of hydroxyl, cyano and halo. In a further subclass of the invention, $R^2$ is pyridinyl wherein said pyridinyl group is optionally substituted with one to two substituents independently selected from the group consisting of cyano and halo.

Reference to the preferred embodiments set forth above is meant to include all combinations of particular and preferred groups unless stated otherwise.

Specific embodiments of the present invention include, but are not limited to:

9-bromo-2-(2-chloro-6-fluorophenyl)-3,6-dihydro-7H-benzo[h]imidazo[4,5-f]isoquinolin-7-one;

9-bromo-2-cyclopentyl-3,6-dihydro-7H-benzo[h]imidazo [4,5-f]isoquinolin-7-one;

9-bromo-2-(2-chlorophenyl)-3,6-dihydro-7H-benzo[h]imidazo[4,5-f]isoquinolin-7-one;

2-cyclopentyl-9-(isobutylamino)-3,6-dihydro-7H-benzo[h] imidazo[4,5-f]isoquinolin-7-one;

2-cyclopentyl-N-[2-(dimethylamino)ethyl]-7-oxo-6,7-dihydro-3H-benzo[h]imidazo[4,5-f]isoquinoline-9-carboxamide;

2-cyclopentyl-9-(1-methyl-1H-pyrazol-4-yl)-3,6-dihydro-7H-benzo[h]imidazo[4,5f]isoquinolin-7-one;

2-(2-chloro-6-fluorophenyl)-9-(6-chloropyridin-3-yl)-3,6-dihydro-7H-benzo[h]imidazo[4,5-f]isoquinolin-7-one;

N'-[2-(2-chloro-6-fluorophenyl)-7-oxo-6,7-dihydro-3H-benzo[h]imidazo[4,5-f]isoquinolin-4-yl]-N,N-dimethylsulfamide;

2-(2,6-difluorophenyl)-9-[(tetrahydrofuran-3-ylmethyl) amino]-3,6-dihydro-7H-benzo[h]imidazo[4,5-f]isoquinolin-7-one;

9-(5-chloropyridin-2-yl)-2-(2,6-difluorophenyl)-3,6-dihydro-7H-benzo[h]imidazo[4,5-f]isoquinolin-7-one;

2-(2-chloro-6-fluorophenyl)-9-(2,6-difluoropyridin-3-yl)-3, 6-dihydro-7H-benzo[h]imidazo[4,5-f]isoquinolin-7-one;

9-bromo-2-(2-chlorophenyl)-3,6-dihydro-7H-benzo[h]imidazo[4,5-f]isoquinolin-7-one;

9-bromo-2-(tetrahydro-2H-pyran-4-yl)-3,6-dihydro-7H-benzo[h]imidazo[4,5-f]isoquinolin-7-one;

9-bromo-2-(tetrahydrofuran-3-yl)-3,6-dihydro-7H-benzo[h] imidazo[4,5-f]isoquinolin-7-one;

9-bromo-2-(tetrahydro-2H-pyran-3-yl)-3,6-dihydro-7H-benzo[h]imidazo[4,5-f]isoquinolin-7-one;

9-bromo-2-(2,2-dimethyltetrahydro-2-H-pyran-4-yl)-3,6-dihydro-7H-benzo[h]imidazo[4,5-f]isoquinolin-7-one;
9-bromo-2-(1-isopropyl-1H-pyrazol-4-yl)-3,6-dihydro-7H-benzo[h]imidazo[4,5-f]isoquinolin-7-one;
9-bromo-2-pyridin-3-yl-3,6-dihydro-7H-benzo[h]imidazo[4,5ف]isoquinolin-7-one;
9-bromo-2-(1,5-dimethyl-1H-pyrazol-4-yl)-3,6-dihydro-7H-benzo[h]imidazo[4,5-f]isoquinolin-7-one;
9-bromo-2-isoquinolin-8-yl-3,6-dihydro-7H-benzo[h]imidazo[4,5-f]isoquinolin-7-one;
9-bromo-2-isoquinolin-5-yl-3,6-dihydro-7H-benzo[h]imidazo[4,5-f]isoquinolin-7-one;
9-bromo-2-cyclopentyl-3,6-dihydro-7H-benzo[h]imidazo[4,5-f]isoquinolin-7-one;
9-bromo-2-(2-chloro-6-fluorophenyl)-3,6-dihydro-7H-benzo[h]imidazo[4,5-f]isoquinolin-7-one;
9-bromo-2-(3-chloropyridin-4-yl)-3,6-dihydro-7H-benzo[h]imidazo[4,5-f]isoquinolin-7-one;
9-bromo-2-(1-phenylethyl)-3,6-dihydro-7H-benzo[h]imidazo[4,5-f]isoquinolin-7-one;
9-bromo-2-(2-chloro-4-fluorophenyl)-3,6-dihydro-7H-benzo[h]imidazo[4,5-f]isoquinolin-7-one;
9-bromo-2-(2,4,6-trifluorophenyl)-3,6-dihydro-7H-benzo[h]imidazo[4,5-f]isoquinolin-7-one;
9-bromo-2-(2,6-difluorophenyl)-3,6-dihydro-7H-benzo[h]imidazo[4,5-f]isoquinolin-7-one;
9-bromo-2-(trifluoromethyl)-3,6-dihydro-7H-benzo[h]imidazo[4,5-f]isoquinolin-7-one;
2-cyclopentyl-9-(isobutylamino)-3,6-dihydro-7H-benzo[h]imidazo[4,5-f]isoquinolin-7-one;
2-cyclopentyl-9-{[(1,5-dimethyl-1H-pyrazol-3-yl)methyl]amino}-3,6-dihydro-7H-benzo[h]imidazo[4,5-f]isoquinolin-7-one;
9-{[1-(4-chlorophenyl)ethyl]amino}-2-cyclopentyl-3,6-dihydro-7H-benzo[h]imidazo[4,5-f]isoquinolin-7-one;
2-cyclopentyl-9-[(tetrahydrofuran-2-ylmethyl)amino]-3,6-dihydro-7H-benzo[h]imidazo[4,5-f]isoquinolin-7-one;
2-cyclopentyl-9-[(2-methoxyethyl)amino]-3,6-dihydro-7H-benzo[h]imidazo[4,5-f]isoquinolin-7-one;
2-cyclopentyl-9-[(2-hydroxy-2-phenylethyl)(methyl)amino]-3,6-dihydro-7H-benzo[h]imidazo[4,5-f]isoquinolin-7-one;
2-cyclopentyl-9-[(2R)-2-phenylmorpholin-4-yl]-3,6-dihydro-7H-benzo[h]imidazo[4,5-f]isoquinolin-7-one;
2-cyclopentyl-9-[(3R)-3-methoxypyrrolidin-1-yl]-3,6-dihydro-7H-benzo[h]imidazo[4,5-f]isoquinolin-7-one;
2-(2,6-difluorophenyl)-9-[(tetrahydrofuran-2-ylmethyl)amino]-3,6-dihydro-7H-benzo[h]imidazo[4,5-f]isoquinolin-7-one;
N'-[2-(2-chloro-6-fluorophenyl)-7-oxo-6,7-dihydro-1H-benzo[h]imidazo[4,5-f]isoquinolin-9-yl]-N,N-dimethylsulfamide;
2-(2,6-difluorophenyl)-9-{[(3-methyloxetan-3-yl)methyl]amino}-3,6-dihydro-7H-benzo[h]imidazo[4,5f]isoquinolin-7-one;
2-(2,6-difluorophenyl)-9-[(tetrahydrofuran-3-ylmethyl)amino]-3,6-dihydro-7H-benzo[h]imidazo[4,5-f]isoquinolin-7-one;
2-(2,6-difluorophenyl)-9-{[(2-methyltetrahydrofuran-2-yl)methyl]amino}-3,6-dihydro-7H-benzo[h]imidazo[4,5-f]isoquinolin-7-one;
2-(2,6-difluorophenyl)-9-[(1,4-dioxan-2-ylmethyl)amino]-3,6-dihydro-7H-benzo[h]imidazo[4,5-f]isoquinolin-7-one;
3-{[2-(2,6-difluorophenyl)-7-oxo-6,7-dihydro-3H-benzo[h]imidazo[4,5-f]isoquinolin-9-yl]amino}propanenitrile;
2-(2,6-difluorophenyl)-9-{[2-(1H-imidazol-4-yl)ethyl]amino}-3,6-dihydro-7H-benzo[h]imidazo[4,5-f]isoquinolin-7-one;
9-[(2,4-difluorobenzyl)amino]-2-(2,6-difluorophenyl)-3,6-dihydro-7H-benzo[h]imidazo[4,5-f]isoquinolin-7-one;
2-(2,6-difluorophenyl)-9-{[2-(pyridin-2-ylamino)ethyl]amino}-3,6-dihydro-7H-benzo[h]imidazo[4,5-f]isoquinolin-7-one;
2-(2,6-difluorophenyl)-9-[(2,3-dihydroxypropyl)amino]-3,6-dihydro-7H-benzo[h]imidazo[4,5-f]isoquinolin-7-one;
2-(2-chlorophenyl)-9-(1-methyl-1H-pyrazol-4-yl)-3,6-dihydro-7H-benzo[h]imidazo[4,5-f]isoquinolin-7-one;
2-(2-chlorophenyl)-9-pyridin-4-yl-3,6-dihydro-7H-benzo[h]imidazo[4,5-f]isoquinolin-7-one;
tert-butyl 4-{4-[2-(2-chlorophenyl)-7-oxo-6,7-dihydro-3H-benzo[h]imidazo[4,5-f]isoquinolin-9-yl]phenyl}piperazine-1-carboxylate;
2-(2-chlorophenyl)-9-(4-piperazin-1-ylphenyl)-3,6-dihydro-7H-benzo[h]imidazo[4,5-f]isoquinolin-7-one;
2-(2-chlorophenyl)-9-[3-(dimethylamino)phenyl]-3,6-dihydro-7H-benzo[h]imidazo[4,5-f]isoquinolin-7-one;
9-biphenyl-3-yl-2-(2-chlorophenyl)-3,6-dihydro-7H-benzo[h]imidazo[4,5-f]isoquinolin-7-one;
9-biphenyl-2-yl-2-(2-chlorophenyl)-3,6-dihydro-7H-benzo[h]imidazo[4,5-f]isoquinolin-7-one;
2-(2-chlorophenyl)-9-pyridin-3-yl-3,6-dihydro-7H-benzo[h]imidazo[4,5-f]isoquinolin-7-one;
4-[2-(2-chlorophenyl)-7-oxo-6,7-dihydro-3H-benzo[h]imidazo[4,5-f]isoquinolin-9-yl]-N,N-dimethylbenzamide;
4-[2-(2-chlorophenyl)-7-oxo-6,7-dihydro-3H-benzo[h]imidazo[4,5-f]isoquinolin-9yl]-N-[2-(dimethylamino)ethyl]benzamide;
2-(2-chlorophenyl)-9-{4-[(4-methylpiperazin-1-yl)carbonyl]phenyl}-3,6-dihydro-7H-benzo[h]imidazo[4,5 -f]isoquinolin-7-one;
2-(2-chlorophenyl)-9-[2-(4-methylpiperazin-1yl)pyridin-4-yl]-3,6-dihydro-7H-benzo[h]imidazo[4,5-f]isoquinolin-7-one;
2-(2-chlorophenyl)-9-[4-(morpholin-4-ylcarbonyl)phenyl]-3,6-dihydro-7H-benzo[h]imidazo[4,5-f]isoquinolin-7-one;
N-{3-[2-(2-chlorophenyl)-7-oxo-6,7-dihydro-3H-benzo[h]imidazo[4,5-f]isoquinolin-9-yl]phenyl}methanesulfonamide;
N-{4-[2-(2-chlorophenyl)-7-oxo-6,7-dihydro-3H-benzo[h]imidazo[4,5-f]isoquinolin-9-yl]phenyl}methanesulfonamide;
2-(2-chlorophenyl)-9-(4-methoxyphenyl)-3,6-dihydro-7H-benzo[h]imidazo[4,5-f]isoquinolin-7-one;
2-(2-chlorophenyl)-9-(3-methoxyphenyl)-3,6-dihydro-7H-benzo[h]imidazo[4,5-f]isoquinolin-7-one;
2-(2-chlorophenyl)-9-(2-methoxyphenyl)-3,6-dihydro-7H-benzo[h]imidazo[4,5-f]isoquinolin-7-one;
4-[2-(2-chlorophenyl)-7-oxo-6,7-dihydro-3H-benzo[h]imidazo[4,5f]isoquinolin-9-yl]-N-ethylbenzamide;
4-[2-(2-chlorophenyl)-7-oxo-6,7-dihydro-3H-benzo[h]imidazo[4,5-f]isoquinolin-9-yl]-N-isobutylbenzamide;
2-(2-chlorophenyl)-9-quinolin-5-yl-3,6-dihydro-7H-benzo[h]imidazo[4,5-f]isoquinolin-7-one;
2-(2-chlorophenyl)-9-(1H-pyrazol-3-yl)-3,6-dihydro-7H-benzo[h]imidazo[4,5-f]isoquinolin-7-one;
2-(2-chlorophenyl)-9-[6-(4-methylpiperazin-1-yl)pyridin-3-yl]-3,6-dihydro-7H-benzo[h]imidazo[4,5-f]isoquinolin-7-one;
2-cyclopentyl-9-(1H-pyrazol-3-yl)-3,6-dihydro-7H-benzo[h]imidazo[4,5-f]isoquinolin-7-one;

2-(2-chloro-6-fluorophenyl)-9-[4-(morpholin-4-ylcarbonyl)phenyl]-3,6-dihydro-7H-benzo[h]imidazo[4,5-f]isoquinolin-7-one;
9-(1H-pyrazol-3-yl)-2-(tetrahydrofuran-3-yl)-3,6-dihydro-7H-benzo[h]imidazo[4,5-f]isoquinolin-7-one;
2-cyclopentyl-N-[2-(dimethylamino)ethyl]-7-oxo-6,7-dihydro-3H-benzo[h]imidazo[4,5-f]isoquinoline-9-carboxamide;
2-cyclopentyl-N-(3-methylbutyl)-7-oxo-6,7-dihydro-3H-benzo[h]imidazo[4,5-f]isoquinoline-9-carboxamide;
2-cyclopentyl-9-[(4-methylpiperazin-1-yl)carbonyl]-3,6-dihydro-7H-benzo[h]imidazo[4,5-f]isoquinolin-7-one;
2-cyclopentyl-9-(morpholin-4-ylcarbonyl)-3,6-dihydro-7H-benzo[h]imidazo[4,5-f]isoquinolin-7-one;
2-cyclopentyl-9-[(4-hydroxypiperidin-1-yl)carbonyl]-3,6-dihydro-7H-benzo[h]imidazo[4,5-f]isoquinolin-7-one;
2-cyclopentyl-9-(piperidin-1-ylcarbonyl)-3,6-dihydro-7H-benzo[h]imidazo[4,5-f]isoquinolin-7-one;
2-cyclopentyl-7-oxo-N-(pyridin-2-ylmethyl)-6,7-dihydro-3H-benzo[h]imidazo[4,5-f]isoquinoline-9-carboxamide;
2-cyclopentyl-7-oxo-N-(pyridin-3-ylmethyl)-6,7-dihydro-3H-benzo[h]imidazo[4,5-f]isoquinoline-9-carboxamide;
2-cyclopentyl-N-(methylsulfonyl)-7-oxo-6,7-dihydro-3H-benzo[h]imidazo[4,5-f]isoquinoline-9-carboxamide;
N-benzyl-2-cyclopentyl-7-oxo-6,7-dihydro-3H-benzo[h]imidazo[4,5-f]isoquinoline-9-carboxamide;
9-(1H-pyrazol-3-yl)-2-(tetrahydrofuran-3-yl)-3,6-dihydro-7H-benzo[h]imidazo[4,5-f]isoquinolin-7-one;
2-cyclopentyl-9-(6-methoxypyridin-3-yl)-3,6-dihydro-7H-benzo[h]imidazo[4,5-f]isoquinolin-7-one;
2-cyclopentyl-9-(1H-pyrazol-4-yl)-3,6-dihydro-7H-benzo[h]imidazo[4,5-f]isoquinolin-7-one;
2-cyclopentyl-9-(2,6-dimethoxypyridin-3-yl)-3,6-dihydro-7H-benzo[h]imidazo[4,5-f]isoquinolin-7-one;
2-cyclopentyl-9-pyrimidin-5-yl-3,6-dihydro-7H-benzo[h]imidazo[4,5-f]isoquinolin-7-one;
2-cyclopentyl-9-(3,5-dimethylisoxazol-4-yl)-3,6-dihydro-7H-benzo[h]imidazo[4,5-f]isoquinolin-7-one;
2-(2-chloro-6-fluorophenyl)-9-(1H-pyrazol-3-yl)-1,6-dihydro-7H-benzo[h]imidazo[4,5-f]isoquinolin-7-one;
2-(2-chloro-6-fluorophenyl)-9-(1H-pyrazol-4-yl)-3,6-dihydro-7H-benzo[h]imidazo[4,5-f]isoquinolin-7-one;
2-(2-chloro-6-fluorophenyl)-9-pyridin-3-yl-1,6-dihydro-7H-benzo[h]imidazo[4,5-f]isoquinolin-7-one;
2-(2-chloro-6-fluorophenyl)-9-(4-morpholin-4-ylphenyl)-3,6-dihydro-7H-benzo[h]imidazo[4,5-f]isoquinolin-7-one;
2-(2-chloro-6-fluorophenyl)-9-(2-morpholin-4-ylpyridin-4-yl)-3,6-dihydro-7H-benzo[h]imidazo[4,5-f]isoquinolin-7-one;
2-(2-chloro-6-fluorophenyl)-9-pyridin-4-yl-3,6-dihydro-7H-benzo[h]imidazo[4,5-f]isoquinolin-7-one;
9-(6-aminopyridin-3-yl)-2-(2-chloro-6-fluorophenyl)-3,6-dihydro-7H-benzo[h]imidazo[4,5-f]isoquinolin-7-one;
2-(2-chloro-6-fluorophenyl)-9-(6-methoxypyridin-3-yl)-3,6-dihydro-7H-benzo[h]imidazo[4,5-f]isoquinolin-7-one;
2-(2-chloro-6-fluorophenyl)-9-(4-methoxypyridin-3-yl)-3,6-dihydro-7H-benzo[h]imidazo[4,5-f]isoquinolin-7-one;
2-(2-chloro-6-fluorophenyl)-9-{6-[(2-morpholin-4-ylethyl)amino]pyridin-3-yl)}-3,6-dihydro-7H-benzo[h]imidazo[4,5f]isoquinolin-7-one;
2-(2-chloro-6-fluorophenyl)-9-(6-hydroxypyridin-3yl)-3,6-dihydro-7H-benzo[h]imidazo[4,5-f]isoquinolin-7-one;
2-(2-chloro-6-fluorophenyl)-9-(5-chloro-2-methoxypyridin-4-yl)-3,6-dihydro-7H-benzo[h]imidazo[4,5-f]isoquinolin-7-one;
2-(2-chloro-6-fluorophenyl)-9-(6-chloropyridin-3-yl)-3,6-dihydro-7H-benzo[h]imidazo[4,5-f]isoquinolin-7-one;
N-{3-[2-(2-chloro-6-fluorophenyl)-7-oxo-6,7-dihydro-3H-benzo[h]imidazo[4,5-f]isoquinolin-9-yl]pyridin-2-yl}-2,2-dimethylpropanamide;
2-(2-chloro-6-fluorophenyl)-9-[2-(cyclopropylmethoxy)pyridin-3yl]-3,6-dihydro-7H-benzo[h]imidazo[4,5-f]isoquinolin-7-one;
2-(2-chloro-6-fluorophenyl)-9-(6-fluoropyridin-3-yl)-3,6-dihydro-7H-benzo[h]imidazo[4,5-f]isoquinolin-7-one;
5-[2-(2-chloro-6-fluorophenyl)-7-oxo-6,7-dihydro-3H-benzo[h]imidazo[4,5-f]isoquinolin-9-yl]pyridine-2-carbonitrile;
2-(2-chloro-6-fluorophenyl)-9-(2,6-difluoropyridin-3-yl)-3,6-dihydro-7H-benzo[h]imidazo[4,5-f]isoquinolin-7-one;
2-(2-chloro-6-fluorophenyl)-9-(6-methylpyridin-3yl)-3,6-dihydro-7H-benzo[h]imidazo[4,5-f]isoquinolin-7-one;
2-(2-chloro-6-fluorophenyl)-9-pyrimidin-5-yl-3,6-dihydro-7H-benzo[h]imidazo[4,5-f]isoquinolin-7-one;
2-(2-chloro-6-fluorophenyl)-9-quinolin-3-yl-3,6-dihydro-7H-benzo[h]imidazo[4,5-f]isoquinolin-7-one;
2-(2-chloro-6-fluorophenyl)-9-[6-(dimethylamino)pyridin-3-yl]-3,6-dihydro-7H-benzo[h]imidazo[4,5-f]isoquinolin-7-one;
2-(2-chloro-6-fluorophenyl)-9-(3-furyl)-3,6-dihydro-7H-benzo[h]imidazo[4,5-f]isoquinolin-7-one;
2-(2-chloro-6-fluorophenyl)-9-(1-methyl-1H-pyrazol-4-yl)-3,6-dihydro-7H-benzo[h]imidazo[4,5-f]isoquinolin-7-one;
9-(4-aminophenyl)-2-(2-chloro-6-fluorophenyl)-3,6-dihydro-7H-benzo[h]imidazo[4,5-f]isoquinolin-7-one;
9-(3-aminophenyl)-2-(2-chloro-6-fluorophenyl)-3,6-7H-benzo[h]imidazo[4,5-f]isoquinolin-7-one;
2-(2-chloro-6-fluorophenyl)-9-[4-(dimethylamino)phenyl]-3,6-dihydro-7H-benzo[h]imidazo[4,5-f]isoquinolin-7-one;
2-(2-chloro-6-fluorophenyl)-9-{2-[(dimethylamino)methyl]phenyl}-3,6-dihydro-7H-benzo[h]imidazo[4,5-f]isoquinolin-7-one;
2-(2-chloro-6-fluorophenyl)-9-(2,6-dimethoxypyridin-3-yl)-3,6-dihydro-7H-benzo[h]imidazo[4,5f]isoquinolin-7-one;
2-(2-chloro-6-fluorophenyl)-9-(3,5-dimethyl-1H-pyrazol-4-yl)-3,6-dihydro-7H-benzo[h]imidazo[4,5-f]isoquinolin-7-one;
2-(2-chloro-6-fluorophenyl)-9-(1,3,5-trimethyl-1H-pyrazol-4yl)-3,6-dihydro-7H-benzo[h]imidazo[4,5f]isoquinolin-7-one;
2-(2-chloro-6-fluorophenyl)-9-isoquinolin-4-yl-3,6-dihydro-7H-benzo[h]imidazo[4,5-f]isoquinolin-7-one;
2-(2-chloro-6-fluorophenyl)-9-(2-methoxypyrimidin-5-yl)-3,6-dihydro-7H-benzo[h]imidazo[4,5-f]isoquinolin-7-one;
2-(2-chloro-6-fluorophenyl)-9-(6-morpholin-4-ylpyridin-3-yl)-3,6-dihydro-7H-benzo[h]imidazo[4,5-f]isoquinolin-7-one;
2-(2-chloro-6-fluorophenyl)-9-(2-methoxypyridin-3-yl)-3,6-dihydro-7H-benzo[h]imidazo[4,5-f]isoquinolin-7-one;
2-(2-chloro-6-fluorophenyl)-9-(2-fluoroquinolin-3-yl)-3,6-dihydro-7H-benzo[h]imidazo[4,5-f]isoquinolin-7-one;
N-{3-[2-(2-chloro-6-fluorophenyl)-7-oxo-6,7-dihydro-3H-benzo[h]imidazo[4,5-f]isoquinolin-9-yl]phenyl}acetamide;
N-{3-[2-(2-chloro-6-fluorophenyl)-7-oxo-6,7-dihydro-3H-benzo[h]imidazo[4,5-f]isoquinolin-9-yl]phenyl}methanesulfonamide;
N-{4-[2-(2-chloro-6-fluorophenyl)-7-oxo-6,7-dihydro-3H-benzo[h]imidazo[4,5-f]isoquinolin-9-yl]phenyl}methanesulfonamide;

3-[2-(2-chloro-6-fluorophenyl)-7-oxo-6,7-dihydro-3H-benzo[h]imidazo[4,5-f]isoquinolin-9-yl]benzamide;
4-[2-(2-chloro-6-fluorophenyl)-7-oxo-6,7-dihydro-3H-benzo[h]imidazo[4,5-f]isoquinolin-9-yl]benzamide;
2-(2,6-difluorophenyl)-9-(1-methyl-1H-pyrazol-4-yl)-3,6-dihydro-7H-benzo[h]imidazo[4,5-f]isoquinolin-7-one;
2-(2,6-difluorophenyl)-9-(6-fluoropyridin-3-yl)-3,6-dihydro-7H-benzo[h]imidazo[4,5-f]isoquinolin-7-one;
2-(2,6-difluorophenyl)-9-(3,4-difluorophenyl)-3,6-dihydro-7H-benzo[h]imidazo[4,5-f]isoquinolin-7-one;
4-[2-(2,6-difluorophenyl)-7-oxo-6,7-dihydro-3H-benzo[h]imidazo[4,5-f]isoquinolin-9-yl]-2-fluorobenzonitrile;
2-(2,6-difluorophenyl)-9-(2,3,4-trifluorophenyl)-3,6-dihydro-7H-benzo[h]imidazo[4,5-f]isoquinolin-7-one;
2-(2,6-difluorophenyl)-9-(2-fluoropyridin-4-yl)-3,6-dihydro-7H-benzo[h]imidazo[4,5-f]isoquinolin-7-one;
2-(2,6-difluorophenyl)-9-(5-fluoropyridin-3-yl)-3,6-dihydro-7H-benzo[h]imidazo[4,5-f]isoquinolin-7-one;
2-2,6-difluorophenyl)-9-(5-fluoropyridin-2-yl)-3,6-dihydro-7H-benzo[h]imidazo[4,5-f]isoquinolin-7-one;
2-(2,6-difluorophenyl)-9-(3-fluoropyridin-4-yl)-3,6-dihydro-7H-benzo[h]imidazo[4,5-f]isoquinolin-7-one,
9-(2-chloropyridin-4-yl)-2-(2,6-difluorophenyl)-3,6-dihydro-7H-benzo[h]imidazo[4,5-f]isoquinolin-7-one;
2-(2,6-difluorophenyl)-9-(6-fluoropyridin-2-yl)-3,6-dihydro-7H-benzo[h]imidazo[4,5-f]isoquinolin-7-one;
9-(5-chloropyridin-2-yl)-2-(2,6-difluorophenyl)-3,6-dihydro-7H-benzo[h]imidazo[4,5-f]isoquinolin-7-one;
2-(2,6-difluorophenyl)-9-(6-methoxypyridin-2-yl)-3,6-dihydro-7H-benzo[h]imidazo[4,5-f]isoquinolin-7-one;
2-(2,6-difluorophenyl)-9-pyridin-2-yl-3,6-dihydro-7H-benzo[h]imidazo[4,5-f]isoquinolin-7-one;
9-[4-(methylsulfonyl)phenyl]-2-(trifluoromethyl)-3,6-dihydro-7H-benzo[h]imidazo[4,5-f]isoquinolin-7-one;
9-(1-methyl-1H-pyrazol-4-yl)-2-(trifluoromethyl)-3,6-dihydro-7H-benzo[h]imidazo[4,5-f]isoquinolin-7-one;
9-{4-[(4-methylpiperazin-1-yl)carbonyl]phenyl}-2-(trifluoromethyl)-3,6-dihydro-7H-benzo[h]imidazo[4,5-f]isoquinolin-7-one;
9-[2-(4-methylpiperazin-1-yl)pyridin-4-yl]-2-(trifluoromethyl)-3,6-dihydro-7H-benzo[h]imidazo[4,5-f]isoquinolin-7-one;
or a pharmaceutically acceptable salt or stereoisomer thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention.

In addition, the compounds disclosed herein may exist as tautomers and both tautomeric forms are intended to be encompassed by the scope of the invention, even though only one tautomeric structure is depicted. For example the following is within the scope of the instant invention:

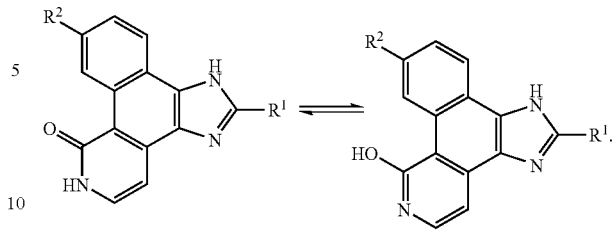

Imidazoles exist as a mixture of 1H/2H tautomers. The tautomeric forms of the imidazole moiety are also within the scope of the instant invention.

When any variable (e.g. $R^3$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to four substituents, and the more preferred embodiment will have from zero to three substituents.

As used herein, "alkyl" is intended to include both branched and straight-chain saturated aliphatic hydrocarbon groups having the specified number of carbon atoms. For example, $C_1$-$C_{10}$ as in "($C_1$-$C_{10}$)alkyl" is defined to include groups having 1, 2, 3, 4, 5, 6, 7, 8, 9 or 10 carbons in a linear or branched arrangement. For example, "($C_1$-$C_{10}$)alkyl" specifically includes methyl, ethyl, n-propyl, i-propyl, n-butyl, t-butyl, i-butyl, pentyl, hexyl, heptyl, octyl, nonyl, decyl, and so on.

The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on.

The term "haloalkyl" means an alkyl radical as defined above, unless otherwise specified, that is substituted with one to five, preferably one to three halogen. Representative examples include, but are not limited to trifluoromethyl, dichloroethyl, and the like.

"Alkoxy" represents either a cyclic or non-cyclic alkyl group of indicated number of carbon atoms attached through an oxygen bridge. "Alkoxy" therefore encompasses the definitions of alkyl and cycloalkyl above.

In certain instances, substituents may be defined with a range of carbons that includes zero, such as $(C_0\text{-}C_6)$alkyl-aryl. If aryl is taken to be phenyl, this definition would include phenyl itself as well as —$CH_2Ph$, —$CH_2CH_2Ph$, $CH(CH_3)$ $CH_2CH(CH_3)Ph$, and so on.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydro-naphthyl, indanyl and biphenyl. In cases where the aryl substituent is bicyclic and one ring is non-aromatic, it is understood that attachment is via the aromatic ring.

The term "heteroaryl," as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively. Such heteroaryl moieties for substituent Q include but are not limited to: 2-benzimidazolyl, 2-quinolinyl, 3-quinolinyl, 4-quinolinyl, 1-isoquinolinyl, 3-isoquinolinyl and 4-isoquinolinyl.

The term "heterocycle" or "heterocyclyl" as used herein is intended to mean a 3- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrathydro analogs thereof. Further examples of "heterocyclyl" include, but are not limited to the following: benzoimidazolyl, benzoimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

As appreciated by those of skill in the art, "halo" or "halogen" as used herein is intended to include chloro (Cl), fluoro (F), bromo (Br) and iodo (I).

Included in the instant invention is the free form of compounds of the instant invention, as well as the pharmaceutically acceptable salts and stereoisomers thereof. Some of the isolated specific compounds exemplified herein are the protonated salts of amine compounds. The term "free form" refers to the amine compounds in non-salt form. The encompassed pharmaceutically acceptable salts not only include the isolated salts exemplified for the specific compounds described herein, but also all the typical pharmaceutically acceptable salts of the free form of compounds of the instant invention. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic (TFA) and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N$^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

Utility

The compounds of the present invention are inhibitors of JAK 1, JAK2, JAK 3, TYK2 and PDK1, and are therefore useful to treat or prevent myeloproliferative disorders or cancer in mammals, preferably humans.

An embodiment of the invention provides a method for inhibiting JAK1 tyrosine kinase, comprising administering to the mammal a therapeutically effective amount of any of the compounds or any of the pharmaceutical compositions described above.

An embodiment of the invention provides a method for inhibiting JAK2 tyrosine kinase, comprising administering to the mammal a therapeutically effective amount of any of the compounds or any of the pharmaceutical compositions described above.

An embodiment of the invention provides a method for inhibiting wild type or mutant JAK2 tyrosine kinase, comprising administering to the mammal a therapeutically effective amount of any of the compounds or any of the pharmaceutical compositions described above.

An embodiment of the invention provides a method for inhibiting JAK2V617F tyrosine kinase, comprising administering to the mammal a therapeutically effective amount of any of the compounds or any of the pharmaceutical compositions described above.

The compounds, compositions and methods provided herein are particularly deemed useful for the treatment of myeloproliferative disorder(s). Myeloproliferative disorders that may be treated include polycythemia vera (PV), essential thrombocythemia (ET), myeloid metaplasia with myelofibrosis (MMM), chronic myelogenous leukemia (CML), myelomonocytic leukemia (CMML), hypereosinophilic syndrome (HES), juvenile myelomonocytic leukemia (JMML), and systemic mast cell disease (SMCD).

It is known in the literature that inhibitors of JAK2 are useful in the treatment and/or prevention of myeloproliferative disorders. See, e.g., Tefferi, A. and Gilliland, D. G. *Mayo Clin. Proc.* 80(7): 947-958 (2005); Fernandez-Luna, J. L. et al. *Haematologica* 83(2): 97-98 (1998); Harrison, C. N. *Br. J. Haematol.* 130(2): 153-165 (2005); *Leukemia* (2005) 19, 1843-1844; and Tefferi, A. and Barbui, T. *Mayo Clin. Proc.* 80(9): 1220-1232 (2005).

The compounds, compositions and methods provided herein are also deemed useful for the treatment of cancer. Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma; unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma; and Adrenal glands: neuroblastoma. Thus, the term "cancerous cell" as provided herein, includes a cell afflicted by any one of the above-identified conditions.

The compounds, compositions and methods of the invention may also be useful in treating the following disease states: keloids and psoriasis.

Cancers that may be treated by the compounds, compositions and methods of the invention include, but are not limited to: breast, prostate, colon, colorectal, lung, brain, testicular, stomach, pancrease, skin, small intestine, large intestine, throat, head and neck, oral, bone, liver, bladder, kidney, thyroid and blood.

Cancers that may be treated by the compounds, compositions and methods of the invention include: breast, prostate, colon, ovarian, colorectal and lung (non-small cell lung).

Cancers that may be treated by the compounds, compositions and methods of the invention include: breast, colon, colorectal and lung.

Cancers that may be treated by the compounds, compositions and methods of the invention include: lymphoma and leukemia.

The compounds of the instant invention are also inhibitors of the activity of PDK1 and are thus useful in the treatment of cancer, in particular cancers associated with deregulated activity of the PTEN/PI3K pathway including, but not limited to PTEN loss of function mutations and receptor tyrosine kinase gain of function mutations. Such cancers include, but are not limited to, ovarian, pancreatic, breast and prostate cancer, as well as cancers (including glioblastoma) where the tumor suppressor PTEN is mutated. See, Feldman, Richard I., et al., "Novel Small Molecule Inhibitors of 3-Phosphoinositide-dependent Kinase-1," *The Journal of Biological Chemistry*, Vol. 280, No. 20, Issue of May 20, pp. 19867-19874, 2005.

PDK1 signaling regulates multiple critical steps in angiogenesis. See, Mora, Alfonso et al., "PDK1, the master regulator of AGC kinase signal transduction," *Seminars in Cell & Developmental Biology* 15 (2004) 161-170. The utility of angiogenesis inhibitors in the treatment of cancer is known in the literature, see J. Rak et al. *Cancer Research*, 55:4575-4580, 1995 and Dredge et al., *Expert Opin. Biol. Ther.* (2002) 2(8):953-966, for example. The role of angiogenesis in cancer has been shown in numerous types of cancer and tissues: breast, carcinoma (G. Gasparini and A. L. Harris, *J. Clin. Oncol.*, 1995, 13:765-782; M. Toi et al., *Japan. J. Cancer Res.*, 1994, 85:1045-1049); bladder carcinomas (A. J. Dickinson et al., *Br. J. Urol.*, 1994, 74:762-766); colon carcinomas (L. M. Ellis et al., *Surgery*, 1996, 120(5):871-878); and oral cavity tumors (J. K. Williams et al., *Am. J. Surg.*, 1994, 168:373-380). Other cancers include, advanced tumors, hairy cell leukemia, melanoma, advanced head and neck, metastatic renal cell, non-Hodgkin's lymphoma, metastatic breast, breast adenocarcinoma, advanced melanoma, pancreatic, gastric, glioblastoma, lung, ovarian, non-small cell lung, prostate, small cell lung, renal cell carcinoma, various solid tumors, multiple myeloma, metastatic prostate, malignant glioma, renal cancer, lymphoma, refractory metastatic disease, refractory multiple myeloma, cervical cancer, Kaposi's sarcoma, recurrent anaplastic glioma, and metastatic colon cancer (Dredge et al., *Expert Opin. Biol Ther.* (2002) 2(8): 953-966). Thus, the PDK1 inhibitors disclosed in the instant application are also useful in the treatment of these angiogenesis related cancers.

Tumors which have undergone neovascularization show an increased potential for metastasis. In fact, angiogenesis is essential for tumor growth and metastasis. (S. P. Cunningham, et al., *Can. Research*, 61: 3206-3211 (2001)). The PDK1 inhibitors disclosed in the present application are therefore also useful to prevent or decrease tumor cell metastasis.

Further included within the scope of the invention is a method of treating or preventing a disease in which angiogenesis is implicated, which is comprised of administering to a mammal in need of such treatment a therapeutically effective amount of a compound of the present invention. Ocular neovascular diseases are an example of conditions where much of the resulting tissue damage can be attributed to aberrant infiltration of blood vessels in the eye (see WO 00/30651, published 2 Jun. 2000). The undesireable infiltration can be triggered by ischemic retinopathy, such as that resulting from diabetic retinopathy, retinopathy of prematurity, retinal vein occlusions, etc., or by degenerative diseases, such as the choroidal neovascularization observed in age-related macular degeneration. Inhibiting the growth of blood vessels by administration of the present compounds would therefore prevent the infiltration of blood vessels and prevent or treat diseases where angio genesis is implicated, such as ocular diseases like retinal vascularization, diabetic retinopathy, age-related macular degeneration, and the like.

Further included within the scope of the invention is a method of treating or preventing a non-malignant disease in which angiogenesis is implicated, including but not limited to: ocular diseases (such as, retinal vascularization, diabetic retinopathy and age-related macular degeneration), atherosclerosis, arthritis, psoriasis, obesity and Alzheimer's disease (Dredge et al., *Expert Opin. Biol. Ther.* (2002) 2(8):953-966). In another embodiment, a method of treating or preventing a disease in which angiogenesis is implicated includes: ocular diseases (such as, retinal vascularization, diabetic retinopathy and age-related macular degeneration), atherosclerosis, arthritis and psoriasis.

Further included within the scope of the invention is a method of treating hyperproliferative disorders such as restenosis, inflammation, autoimmune diseases and allergy/asthma.

Further included within the scope of me instant invention is the use of the instant compounds to coat stents and therefore the use of the instant compounds on coated stents for the treatment and/or prevention of restenosis (WO03/032809).

Further included within the scope of the instant invention is the use of the instant compounds for the treatment and/or prevention of osteoarthritis (WO03/035048).

Further included within the scope of the invention is a method of treating hypoinsulinism.

An embodiment of the invention provides a method for inhibiting JAK3 tyrosine kinase, comprising administering to the mammal a therapeutically effective amount of any of the compounds or any of the pharmaceutical compositions described above.

An embodiment of the invention provides a method for inhibiting TYK2 tyrosine kinase, comprising administering to the mammal a therapeutically effective amount of any of the compounds or any of the pharmaceutical compositions described above.

Exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of: bone loss, bone resorption, bone fractures, metastatic bone disease and/or disorders related to cathepsin functioning.

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating-agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable, emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the instant invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compounds of the instant invention are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

When a composition according to this invention is administered into a human subject, the daily dosage will normally be determined by the prescribing physician with the dosage generally varying according to the age, weight, and response of the individual patient, as well as the severity of the patient's symptoms.

In an embodiment, a suitable amount of an inhibitor of JAK2 is administered to a mammal undergoing treatment for cancer. Administration occurs in an amount of inhibitor of between about 0.1 mg/kg of body weight to about 60 mg/kg of body weight per day, or between 0.5 mg/kg of body weight to about 40 mg/kg of body weight per day. Another therapeutic dosage that comprises the instant composition includes from about 0.01 mg to about 1000 mg of inhibitor of JAK2. In another embodiment, the dosage comprises from about 1 mg to about 1000mg of inhibitor of JAK2.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5, 6-pentafluoro-N-(3-fluoro-4-methoxyphenyl) benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797. In an embodiment the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino] ethyl]-5-[4-hydro0xy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino] benzo[g]isoguinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c] quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589, 485, 5,602,098, European Patent Publ. 0 618 221, European Patent Publ. 0 675 112, European Patent Publ. 0 604 181, European Patent Publ: 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1(VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107. (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 911.6 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141-145 (1985)), and antibodies to VEGF (see, Nature Biotechnology, Vol. 17, pp.963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in Clin. Chem. La. Med. 38:679-692 (2000)). Examples of such agents that modulate or inhibit the coagulation and fibrinolysis pathways include, but are not limited to, heparin (see Thromb. Haemost. 80:10-23 (1998)), low molecular weight heparins and carboxypeptidase U inhibitors (also known as inhibitors of active thrombin activatable fibrinolysis inhibitor [TAFIa]) (see Thrombosis Res. 101:329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK11 and CHK12 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, Nature, 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, U.S. Ser. Nos. 60/734188, 60/652737, 60/670469), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 μM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. Nos. 5,344,991, 5,134,142, 5,380,738, 5,393,790, 5,466,823, 5,633,272 and 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide,CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the αvβ5 integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl]indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis (2-methoxyethoxy)-4-quinazolinamine, BIBX1382, 2,3,9, 10,11,12-hexahydro-10-(hydroxymethyl)-10-hydroxy-9-methyl-9,12-epoxy-1H-diindolo[1,2,3-fg:3',2',1'-kl]pyrrolo [3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999,274: 9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy) phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (Cancer Medicine, 5th Ed, pp 876-889, B C Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998;5(8):1105-13), and interferon gamma (*J. Immunol.* 2000;164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232, 929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913,0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959,0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099,93/09116, 93/10073, 93/14084, 93/14113, 93/18023, 93/19064, 93/21155, 93/21181, 93/23380,93/ 24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017,95/ 15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317,96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2,269 590, 2 271 774 74, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

A compound of the instant invention may also be useful for treating or preventing cancer in combination with inhibitors of Akt. Such inhibitors include compounds described in, but not limited to, the following publications: WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734188, 60/652737, 60/670469.

A compound of the instant invention may also be useful for treating or preventing cancer in combination with PARP inhibitors.

A compound of the instant invention may also be useful for treating cancer in combination with the following therapeutic agents: abarelix (Plenaxis depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); and zoledronate (Zometa®).

Thus, the scope of the instant invention encompasses the use of the instantly claimed compounds in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

Also included in the scope of the claims is a method of treating cancer that comprises administering a therapeutically effective amount of a compound of the instant invention in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

The instant invention also includes a pharmaceutical composition useful for treating or preventing cancer that comprises a therapeutically effective amount of a compound of the instant invention and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

All patents, publications and pending patent applications identified are hereby incorporated by reference.

Abbreviations used in the description of the chemistry and in the Examples that follow are:

| | |
|---|---|
| $CH_2Cl_2$ | methylene chloride |
| DCM | dichloromethane |
| DMSO | dimethyl sulfoxide |
| EtOAc | ethyl acetate |
| HCl | hydrochloric acid |
| HPLC | high-performance liquid chromatography |
| HRMS | high resolution mass spectrum |
| LRMS | low resolution mass spectrum |
| $MgSO_4$ | magnesium sulfate |
| $NaHCO_3$ | sodium bicarbonate |
| NaOH | sodium hydroxide |
| $Na_2SO_4$ | sodium sulfate |
| NMR | (nuclear magnetic resonance); |
| $Pd_2(dba)_3$ | tris(dibenzylideneacetone) dipalladium(0) |
| SEMCl | 2-(trimethylsilyl)ethoxymethyl chloride |
| TBAF | tetrabutylanunonium fluoride |
| THF | tetrahydrofuran |
| $TiCl_3$ | titanium chloride |

The compounds of the present invention can be prepared according to the following general schemes, using appropriate materials, and are further exemplified by the subsequent specific examples. The compounds illustrated in the examples are not, however, to be construed as forming the only genus that is considered as the invention. The illustrative Examples below, therefore, are not limited by the compounds listed or by any particular substituents employed for illustrative purposes. Those skilled in the art will readily understand that known variations of the conditions and processes of the following preparative procedures can be used to prepare these compounds. All temperatures are degrees Celsius unless otherwise noted.

General procedures to prepare compounds of the instant invention are described in Scheme A. Treatment of 2-fluoro-4-methylpyridine with a base, such as NaHMDS, followed by the addition alkylbenzoate II provides ketone III. Ketone III can be oxidized to oxime IV by the action of an alkyl nitrite. Condensation of IV with an aldehyde (V) and ammonium acetate, by either heating in a conventional manner or in a microwave, leads to imidazoles of structure VI. The hydroxyimidazole can be reduced using a variety of different reducing agents, such as TiCl₃, to furnish VII. Subjection of a solution of VII to a source of high intensity photochemical radiation leads to compounds of the instant invention as embodied by VIII.

SCHEME A

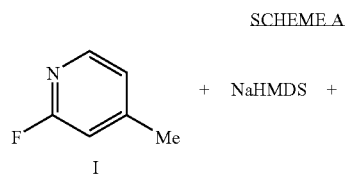

I

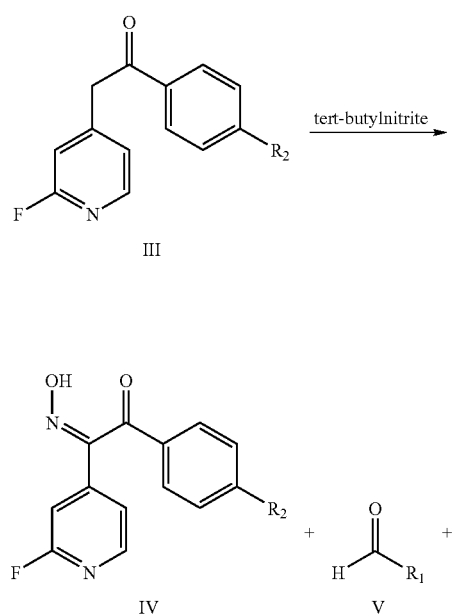

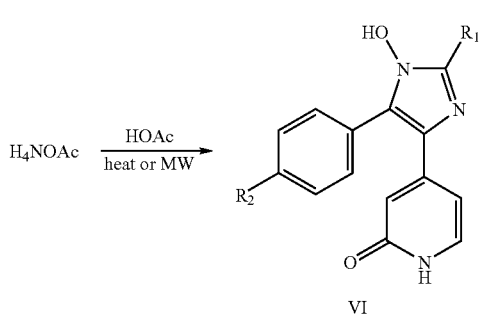

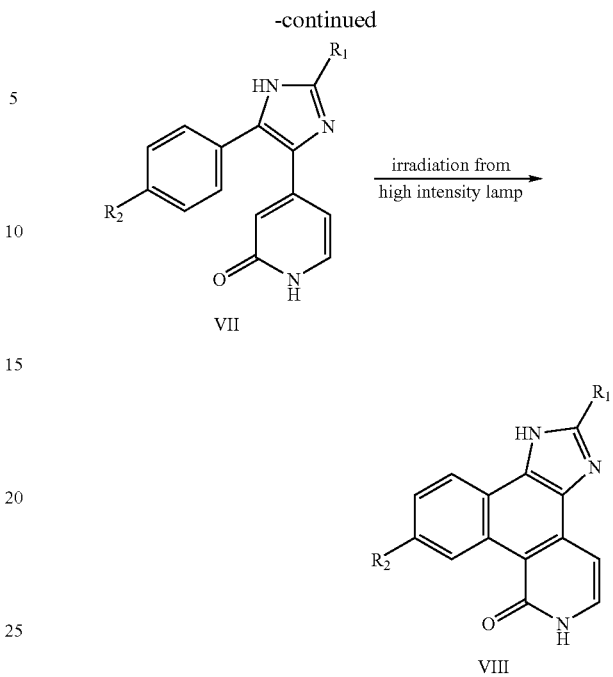

General procedures to prepare compounds of the instant invention are also described in Scheme B. Treatment of bromide VIII with a source of palladium, an amine, and an organic or inorganic base will furnish compounds of the instant invention as embodied by structure IX.

SCHEME B

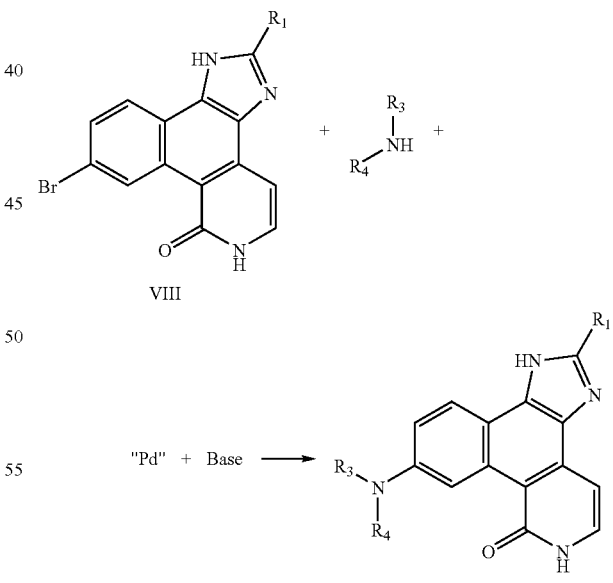

General procedures to prepare compounds of the instant invention are also described in Scheme C. Treatment of bromide VIII with a source of palladium, Mo(CO)₆, and an organic or inorganic base, will furnish compounds of the instant invention as embodied by structure X.

SCHEME C

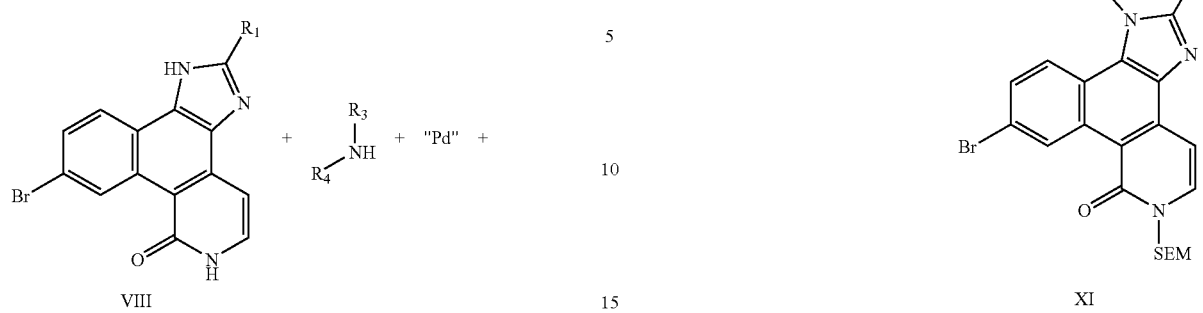

General procedures to prepare compounds of the instant invention are also described in Scheme D. Those skilled in the art synthetic organic chemistry could choose from a suitable list of protecting groups to allow for the preparation of compounds of the instant invention as embodied by sulfonyl-urea XIII in Scheme D. As an example, treatment of compound VIII with a base, such as NaH or tBuOK followed by SEM-Cl, will furnish the bis-SEM material XI. Treatment of bromide XI with a source of palladium, a sulfonyl-urea, and an organic or inorganic base will furnish XII. Removal of the SEM protecting groups under the action of a fluoride source such TBAF, ZnF, or CsF or under acidic treatment such as HCl with or without conventional heating or with a microwave, will provide compounds of the instant invention as embodied by XIII.

SCHEME D

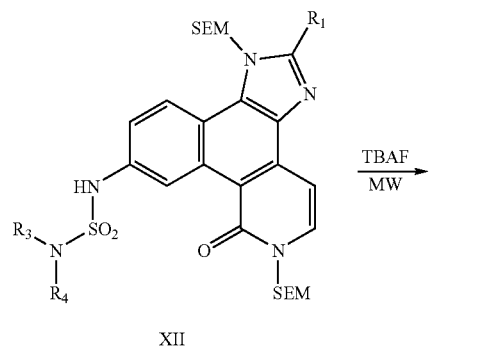

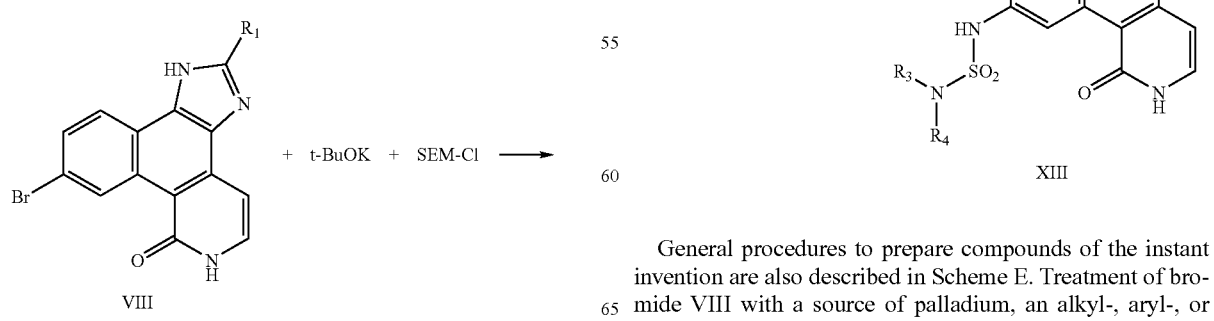

General procedures to prepare compounds of the instant invention are also described in Scheme E. Treatment of bromide VIII with a source of palladium, an alkyl-, aryl-, or heteroarylboronic acid, and an inorganic base furnishes compounds of the instant invention as embodied by structure XIV.

SCHEME E

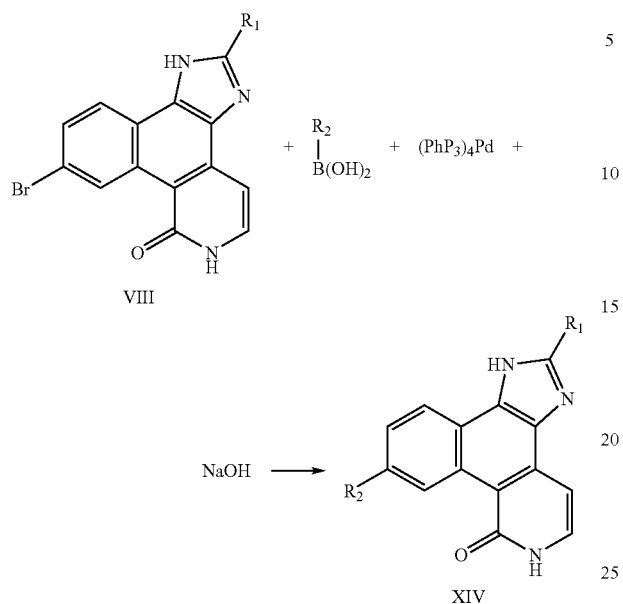

General procedures to prepare compounds of the instant invention are also described in Scheme F. Treatment of bromide VIII with a source of palladium, an alkyl-, aryl-, or heteroarylboronate ester, and an inorganic base furnished the instant invention as embodied by structure XIV.

SCHEME F

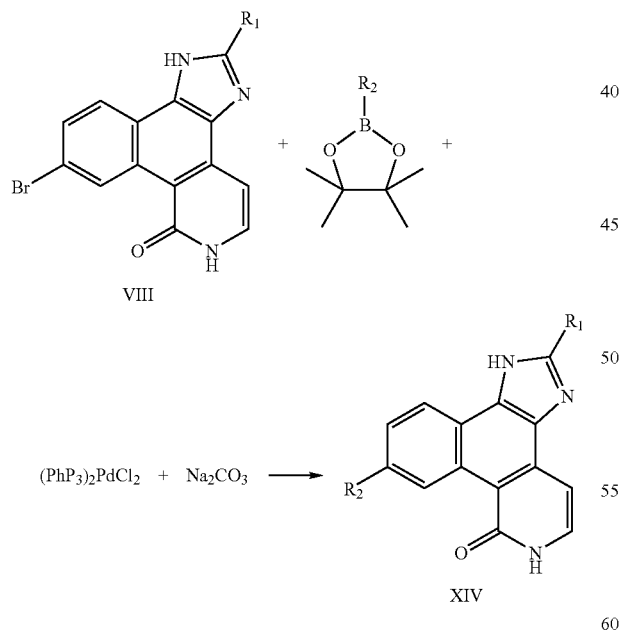

General procedures to prepare compounds of the instant invention are also described in Scheme G. Treatment of bromide VIII with a source of palladium, bis-pinacolborane, and an inorganic base furnishes boronate XV. Treatment of boronate XV with a source of palladium, an aryl- or heteroaryl-halide, $R_2X$, where X is chosen from chloride, bromide, or iodide, or aryl- or heteroaryl-triflate, $R_2X$, and an inorganic base furnishes compounds of the instant invention as embodied by structure XIV.

SCHEME G

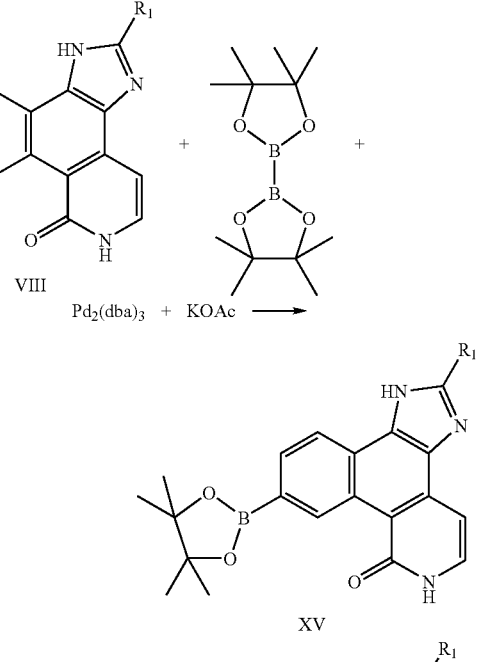

The compounds of this invention may be prepared by employing reactions as shown in the following Examples, in addition to other standard manipulations that are known in the literature or exemplified in the experimental procedures.

EXAMPLE 1

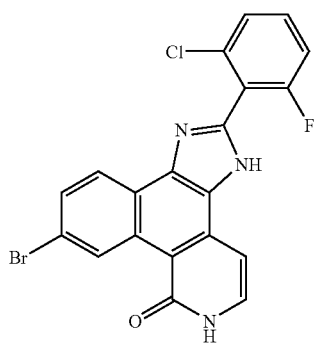

9-Bromo-2-(2-Chloro-6-Fluorophenyl)-3,6-Dihydro-7H-Benzo[H]Imidazo[4,5-F]Isoquinolin-7-One

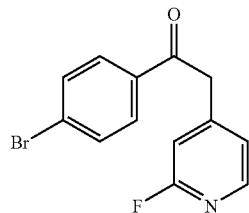

Step A: 1-(4-bromophenyl)-2-(2-fluoropyridin-4-yl)ethanone

To a solution of sodium bis(trimethylsilyl)amide (235 mL, 2M) in THF (750 mL) under nitrogen, cooled to 2° C., was added 2-fluoro-4-methylpyridine (25 g, 0.225 mol) and the solution stirred for 45 minutes in an ice bath. Ethyl 4-bromobenzoate (55 g, 0.239 mol) was added and the reaction was stirred overnight at RT. The reaction mixture was poured into excess aqueous 2N HCl, and the aqueous layer was made basic with 5 N NaOH and extracted with EtOAc. The organic extracts were combined, washed with brine, dried over MgSO$_4$, filtered and concentrated under reduced pressure. The residue was dissolved in CH$_2$Cl$_2$ and filtered through a cotton plug. Hexanes were added and the CH$_2$Cl$_2$ was removed under reduced pressure until precipitation of the title compound occurred as a pale yellow solid. $^1$H NMR (400 MHz, CDCl$_3$): δ8.20 (m, 1H), 7.85 (m, 2H), 7.65 (m, 2H), 7.05 (m, 1H), 6.82 (m, 1H), 4.30(s, 2H).

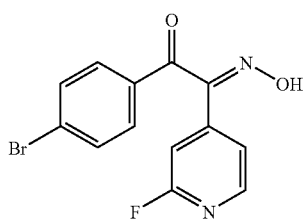

Step B: 1-(4-bromophenyl)-2-(2-fluoropyridin-4-yl)ethane-1,2-dione 2-oxime

To a solution of the intermediate from Example 1 Step A (48 g, 0.163 mol) in ethanol (800 mL) at −10° C. was added dropwise t-butylnitrite (22.1 mL, 0.18 mol) over 10 minutes, followed by 2.5 N HCl in absolute ethanol (52 mL, 0.13 mol). The reaction temperature was maintained at −5° C. during these additions. After the addition was completed, the dry ice bath was removed and the reaction was allowed to warm to RT overnight. The ethanol was removed under reduced pressure and the residue was diluted with H$_2$O. The aqueous phase was made basic with saturated NaHCO$_3$ and extracted with EtOAc. The combined organic extracts were washed with brine, dried over Na$_2$SO$_4$ and concentrated under reduced pressure. The crude residue was taken up in methanol/isopropanol and mixed with toluene. The methanol/isopropanol mixture was concentrated under reduced pressure and the title compound was recrystallized from hexane/toluene. $^1$H NMR (400 MHz, CDCl$_3$): δ8.22 (m, 1H), 7.78 (m, 2H), 7.65 (m, 2H), 7.32 (m, 1H), 7.08(s, 1H).

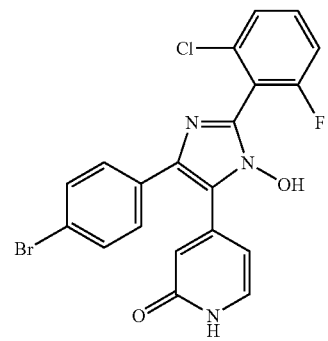

Step C: 4-[4-(4-bromophenyl)-2-(2-chloro-6-fluorophenyl)-1-hydroxy-1H-imidazol-5-yl]pyridin-2(1H)-one To a solution of the intermediate from Example 1 Step 3 (14 g, 0.04 mol) in acetic acid (500 mL) and under nitrogen was added 2-chloro-6-fluorobenzaldehyde (7.9 g, 0.05 mol) and ammonium acetate (62 g, 0.8 mol). The reaction solution was heated to reflux overnight. The acetic acid was removed under reduced pressure and the remaining material was taken up in water. The pH of the solution was adjusted to 8-10 by the addition of solid ammonium hydroxide and then extracted several time with EtOAc. The solvent was removed under reduced pressure and the crude product was dissolved in ethanol twice and concentrated to a small volume under reduced pressure to azeotropically remove water. The title compound was recrystallized from ethanol and hexane. $^1$H NMR (400 MHz, DMSO-d$_6$): δ11.95 (br, 2H), 7.35~7.70 (m, 8H), 6.45 (m, 1H), 6.15 (m, 1H).

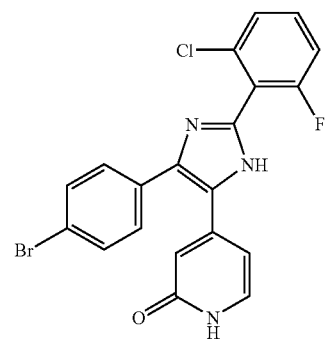

Step D: 4-[4-(4-bromophenyl)-2-(2-chloro-6-fluorophenyl)-1H-imidazol-5-yl]pyridin-2(1H)-one To a solution of the intermediate from Example 1 Step C (11 g, 0.024 mol) in methanol (0.5 L) at 0° C. under nitrogen was added TiCl$_3$ (15~20%, 120 mL) over 45 minutes while maintaining the reaction temperature under 10° C. The solution was warmed to RT and stirred overnight. The volatiles were removed under reduced pressure, and the solution was made basic with saturated NaHCO$_3$ and 5 N NaOH. Ethyl acetate was added and the mixture was stirred overnight. The solution was filtered through a Solka floc pad to remove the solids. The filtrate was extracted with EtOAc and the organic layer was then washed twice with brine, dried over Na$_2$SO$_4$, filtered, and concentrated under reduced pressure to provide the crude residue which was purified by on silica gel (gradient elution with 2%-10% DCM-methanol as an eluant) to yield the title compound. ¹H NMR (300 MHz, DMSO-d6): δ13.12 (m, 1H), 11.45 (br, 1H), 7.22~7.70 (m, 9H), 6.10~6.32 (m, 2H).

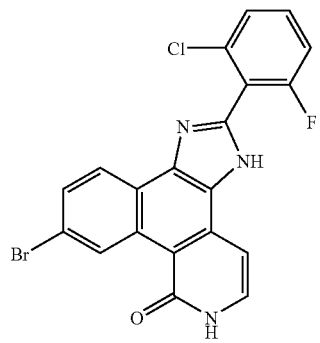

Step E: 9-bromo-2-(2-chloro-6-fluorophenyl)-3,6-dihydro-7H-benzo[h]imidazo[4,5-f]isoquinolin-7-one The intermediate from Example 1 Step D (2.9 g, 6.55 mmol) was dissolved in 200 mL of a 60:40 mixture of 1,2-dichloroethane-ethanol. The mixture was irradiated under a high intensity light for 3 days. The volatiles were removed in vacuo and the crude material was triturated with DCM and filtered. The product was triturated twice more with EtOAc and filtered. ¹ NMR 400 MHz, DMSO-d₆: δ14.12 (br, 1H), 11.82 (m, 1H), 10.55(m, 1H), 7.40~7.90(m, 7H): [M+1]⁺ 442.

EXAMPLE 2

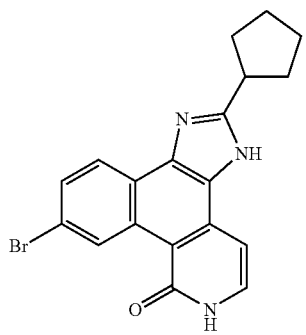

9-Bromo-2-Cyclopentyl-3,6-Dihydro-7H-Benzo[H]Imidazo[4,5-F)]Isoquinolin-7-One

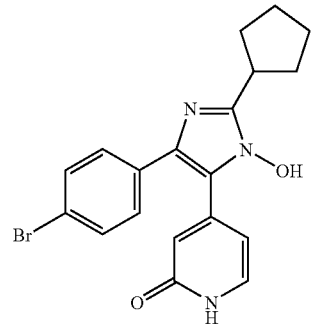

Step A: 4-[4-(4-bromophenyl)-2-cyclopentyl-1-hydroxy-1H-imidazol-5-yl]pyridin-2(1H)-one Using the general procedure found in Example 1 Step C, the intermediate from Example 1 Step B was combined with cyclopentane carboxaldehyde and ammonium acetate and acetic acid. ¹H NMR (400 MHz, DMSO-d₆): δ11.95 (br, 2H), 7.35~7.70 (m, 8H), 6.45 (m, 1H), 6.15 (m, 1H).

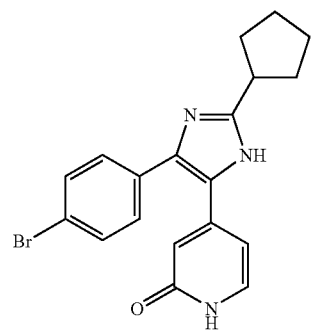

Step B: 4-[4-(4-bromophenyl)-2-cyclopentyl-1H-imidazol-5-yl]pyridin-2(1H)-one

Using the general procedure in Example 1 Step D, the intermediate of Example 2 Step A was treated with TiCl₃ in methanol. ¹H NMR (400 MHz, DMSO-d₆): δ 12.22 (m, 1H), 11.30 (br, H), 7.20~7.65 (m, 5H), 6.0~6.39 (m, 2H), 3.08 (m, 1H), 1.5~1.85 (m,8H).

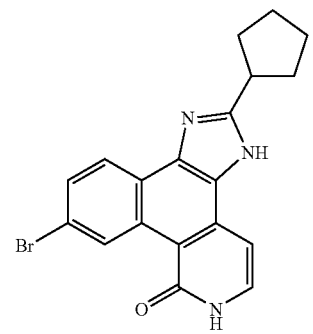

Step C: 9-bromo-2-cyclopentyl-3,6-dihydro-7H-benzo[h]imidazo[4,5-f]isoquinolin-7-one Using the general procedure in Example 1 Step E, the intermediate of Example 2 Step B was was irradiated under a high intensity light in THF. $^1$H NMR (600 MHz, DMSO) δ: 13.18 (s, 1 H), 13.05 (s, 1 H)*, 11.72 (d, J=5.6 Hz, 1 H)*, 11.66 (d, J=5.6 Hz, 1 H), 10.52 (d, J=2.0 Hz , 1 H), 10.44 (d, J=2.0 Hz, 1 H)*, 8.43 (d, J=8.8 Hz, 1 H)*, 8.32 (d, J=8.5 Hz, 1 H), 7.82 (dd, J=8.5, 2.0, 1 H), 7.74 (dd, J=8.8, 2.0 Hz, 1 H)*, 7.61 (m, 1 H)*, 7.52 (m, 1 H), 7.24 (dd, J=6.8, 1.5 Hz, 1 H), 7.14 (dd, J=6.8, 1.5 Hz, 1 H)*, 2.13 (m, 2 H), 2.13 (m, 2 H)*, 1.98 (m, 2 H), 1.98 (m, 2 H)*, 1.82 (m, 2 H), 1.82 (m, 2 H)*, 1.69 (m, 2 H), 1.69 (m, 2 H)* (note: *—denotes peaks derived from the minor tautomer): [M+1]$^+$ 382.

EXAMPLE 3

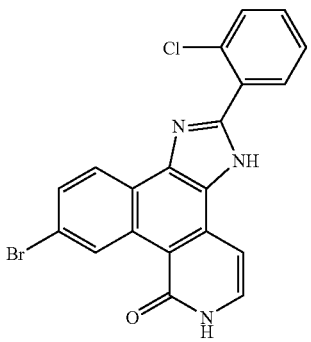

9-Bromo-2-(2-Chlorophenyl)-3,6-Dihydro-7H-Benzo[H]Imidazo[4,5-F]Isoquinolin-7-One Step A: 4-[4-(4-bromophenyl)-2-(2-chlorophenyl)-1-hydroxy-1H-imidazol-5-yl]pyridin-2(1H)-one Using the general procedure found in Example 1 Step C, the intermediate from Example 1 Step B was combined with 2-chlorobenzaldehyde, ammonium acetate and acetic acid.

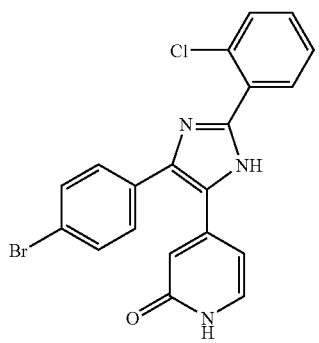

Step B: 4-[4-(4-bromophenyl)-2-(2-chlorophenyl)-1H-imidazol-5-yl]pyridin-2(1H)-one Using the general procedure in Example 1 Step D, the intermediate of Example 3 Step A was treated with TiCl$_3$ in methanol. $^1$H NMR (400 MHz, DMSO-d$_6$): [M+1]$^+$ 427.

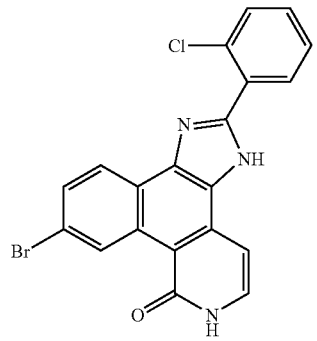

Step C: 9-bromo-2-(2-chlorophenyl)-3,6-dihydro-7H-benzo[h]imidazo[4,5-f]isoquinolin-7-one Using the general procedure in Example 1 Step E, the intermediate of Example 3 Step B was was irradiated under a high intensity light in THF. $^1$H NMR (600 MHz, DMSO) δ: 13.87 (s, 1 H), 13.76 (s, 1 H)*, 11.86 (m, 1 H)*, 11.77 (m, 1 H), 10.55 (d, J=2.0 Hz, 1 H), 10.49 (d, J=2.0 Hz, 1 H)*, 8.49 (d, J=8.5 Hz, 1 H), 8.41 (d, J=8.5 Hz, 1 H)*, 7.88 (m, 1 H), 7.88 (m, 1 H)*, 7.86 (m, 1 H), 7.81 (m, 1 H)*, 7.70 (m, 1 H), 7.70 (m, 1 H)*, 7.57 (m, 3 H), 7.57 (m, 3H)*, 7.31 (m, 1 H), 7.24 (m, 1 H)* (note: * denotes peaks derived from the minor tautomer): [M+1]$^+$ 424.

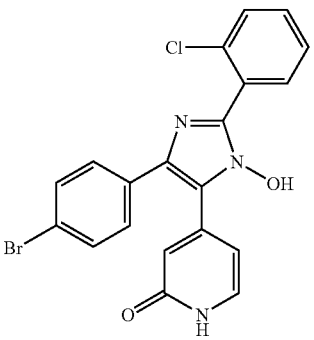

EXAMPLE 4

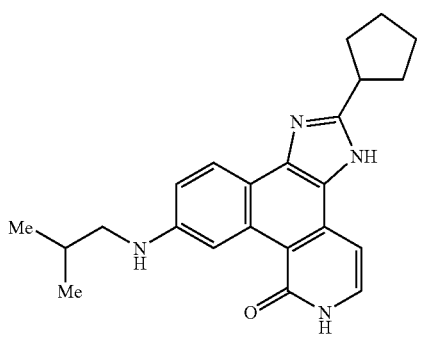

2-Cyclopentyl-9-(Isobutylamino)-3,6-Dihydro-7H-Benzo[H]Imidazo[4,5-F]Isoquinolin-7-One Step A: 2-cyclopentyl-10-(isobutylamino)-3,6-dihydro-7H-benzo[h]imidazo[4,5-f]isoquinolin-7-one A 0.5-2 mL microwave vial containing a stir bar was placed under argon by attaching a rubber septum and performing 4 vacuum/argon cycles. The aryl bromide from Example 2, Step C, (41.8 mg, 0.065 mmol), sodium tert-butoxide (9.4 mg, 0.0975 mmol), 2-(di-tert-butylphosphino)biphenyl (3.9 mg, 0.013 mmol), $Pd_2(dba)_3$ (6.0 mg, 0.0065 mmol) were added, and the vial was sealed. While adding the solids to the vial, 30 mL of toluene was deoxygenated by bubbling argon through for 30 minutes; 0.4 mL of this was added to the sealed reaction vial. Isobutyl amine (0.009 ml, 0.094 mmol) was added via microsyringe, and then argon was flushed gently through the vial for 5 min. The reaction was heated to 100° C. for 24 hours and then cooled to room temperature. A solution of tetrabutylammonium fluoride (1 M in tetrahydrofuran, 0.20 ml, 0.02 mmol) was added, and the vial was heated in a microwave oven for 5 min at 150° C. for 5 min at 170° C. After cooling to room temperature, the reaction mixture was partitioned between a 1:1 mixture of EtOAc:ether (4 mL) and 1:1 water:saturated $NaHCO_3$ (3 mL). The layers were separated, and the organic layer was washed with brine (3 mL), dried over MgSO4, filtered, and concentrated. The resulting solid was purified by reverse phase HPLC. After lyophilization, the title compound was obtained: $[M+1]^+$ 375.

EXAMPLE 5

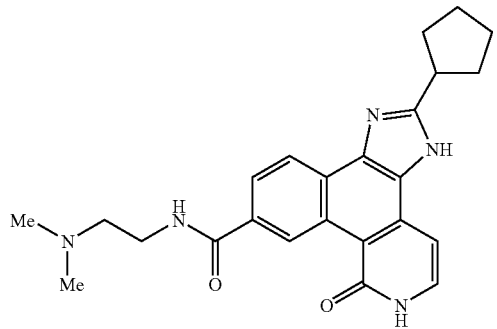

2-Cyclopentyl-N-[2-(Dimethylamino)ethyl]-7-Oxo-6,7-Dihydro-3H-Benzo[H]Imidazo[4,5-F]Isoquinoline-9-Carboxamide Step A: 2-cyclopentyl-N-[2-(dimethylamino)ethyl]-7-oxo-6,7-dihydro-3H-benzo[h]imidazo[4,5-f]isoquinoline-9-carboxamide A 0.5-2 mL microwave vial was charged with a stir bar, aryl bromide from Example 2, Step C; (50 mg, 0.131 mmol), molybdenum hexacarbonyl (34.6 mg, 0.131 mmol), tri-tert-butylphosphine tetrafluoroborate (3.8 mg, 0.013 mmol), and trans-di(mu-acetato)bis[o-(di-o-tolylphosphino)benzyl]dipalladium (II) (6.1 mg, 0.0066 mmol). A solution of 1,8-diazabicyclo[5.4.0]undec-7-ene (0.06 mL, 0.524 mmol) and N,N-dimethylethylenediamine (0.054 mL, 0.393 mmol) in 1,4-dioxane (0.65 mL) was added to the vial, and the vial was sealed. The reaction was then heated in a microwave oven for 15 min at 140° C. After cooling to room temperature, the reaction mixture was transferred to a scintillation vial using methanol and concentrated to dryness. The crude product was purified by reverse phase HPLC which provided the title compound. $^1$H NMR (600 MHz, DMSO) δ: 13.19 (s, 1 H), 13.04 (s, 1 H)*, 11.68 (s, 1H)*, 11.60 (s, 1 H), 10.70 (s ,1 H), 10.64 (s, 1 H)*, 8.50 (s, 1 H)*, 8.38 (m, 2 H), 8.36 (m, 1 H)*, 8.24 (s, 1 H), 8.24 (s, 1 H)*, 8.00 (s, 1 H)*, 7.98 (s, 1 H), 7.58 (s, 1 H)*, 7.50 (s, 1 H), 7.22 (s, 1 H), 7.14 (s, 1 H)*, 3.42 (m, 4 H), 3.42 (m, 4 H)*, 2.22 (s, 6 H), 2.22 (s, 6 H)*, 2.13 (m, 2 H), 2.13 (m, 2 H)*, 1.99 (m, 2 H), 1.99 (m, 2 H)*, 1.82 (m, 2 H), 1.82 (m, 2 H)*, 1.64 (m, 2 H), 1.64 (m, 2 H)* (note: * denotes peaks derived from the minor tautomer): $[M+1]^+$ 418.

EXAMPLE 6

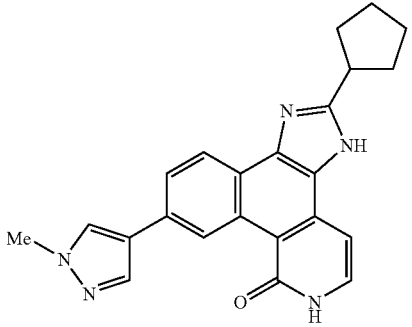

2-Cyclopentyl-9-(1-Methyl-1H-Pyrazol-4-Yl)-3,6-Dihydro-7H-Benzo[H]Imidazo[4,5-F]Isoquinolin-7-One Step A: 2-(2-chlorophenyl)-9-(1-methyl-1H-pyrazol-4-yl)-3,6-dihydro-7H-benzo[h]imidazo[4,5-f]isoquinolin-7-one 9-Bromo-2-(2-chlorophenyl)-3,6-dihydro-7H-benzo[h]imidazo[4,5-f]isoquinolin-7-one (30 mg, 0.071 mmol), lithium chloride (6 mg, 0.14 mmol), 1-methyl-4-(4,4,5,5-tetramethyl-1,3,2-dioxaborolan-2-yl)-1H-pyrazole (30 mg, 0.14 mmol), and tetrakis(triphenylphosphine)palladium(0) (8 mg, 0.0071 mmol) were placed in a microwave tube. $Na_2CO_3$ (2 M, 0.25 mL) and DMF (1 mL) were added and the solution was heated in the microwave at 130° C. for ten minutes. The solution was cooled to ambient temperature diluted with ethyl acetate and Na$_2$CO$_3$ (2 M). The organic layer was separated, washed with brine, dried over MgSO$_4$, filtered and concentrated to dryness. The crude residue was purified on silica gel to afford the title compound. $^1$H NMR (500 MHz, DMSO-d$_6$, δ$_H$) 11.56 (bs, 1 H), 10.49 (bs, 1 H), 8.56-8.45 (m, 1 H), 8.18 (s, 1 H), 7.90-7.87 (m, 3 H), 7.69 (d, 1 H, J=7.2 Hz), 7.58-7.54 (m, 3H), 7.34-7.28 (m, 1 H): [M+1]$^+$ 426.1.

EXAMPLE 7

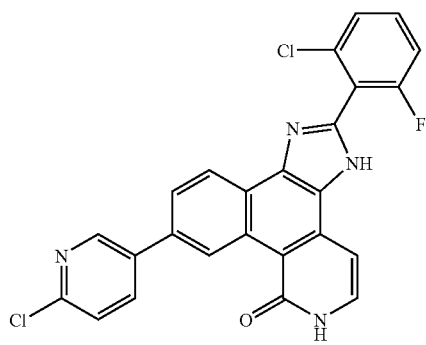

2-(2-Chloro-6-Fluorophenyl)-9-(6-Chloropyridin-3-Yl)-3,6-Dihydro-7H-Benzo[H]Imidazo[4,5-F]Isoquinolin-7-One Step A: 2-(2-chloro-6-fluorophenyl)-9-(6-chloropyridin-3-yl)-3,6-dihydro-7H-benzo[h]imidazo[4,5-f]isoquinolin-7-one 9-Bromo-2-(2-chloro-6-fluorophenyl)-3,6-dihydro-7H-benzo[h]imidazo[4,5-f]isoquinolin-7-one (500 mg, 1.130 mmol) was dissolved in ethanol (15 ml) and toluene (15.00 ml). (Dichlorobis)palladiumtriphenylphosphine (79 mg, 0.113 mmol), 2-chloro-5-(4,4,5,5-tetramethyl-1,3,2-dioxaborolan-2-yl)pyridine (298 mg, 1.242 mmol) and Na$_2$CO$_3$ (2 M, 1.135 mL) were added and argon was bubbled through the solution for several minutes. The solution was heated at 80° C. for 2 hours. The reaction mixture was cooled to ambient temperature and diluted with ethyl acetate and water. The organic layer was separated, dried over magnesium sulftate, filtered and concentrated. The crude residue was purified via a chiral AD column which afforded the title compound. $^1$H NMR (500 MHz, CD$_3$OD, δ$_H$) 10.68 (s, 1 H), 8.56 (d, 1 H, J=1.8 Hz), 8.30 (dd, 1 H, J=8.4, 3.0 Hz), 8.04 (dd, 1 H) J=9.0, 1.8 Hz), 7.68-7.64 (m, 1 H), 7.63-7.60 (m, 2 H), 7.54 (d, 1 H, J=8.4 Hz), 7.38 (td, 1 H, J =9, 1.2 Hz): [M+1]$^+$ 475.

EXAMPLE 8

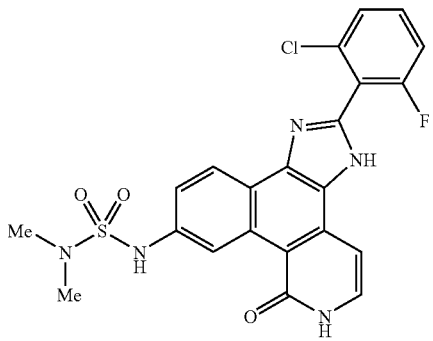

N'-[2-(2-Chloro-6-Fluorophenyl)-7-Oxo-6,7-Dihydro-3H-Benzo[H]Imidazo[4,5-F]Isoquinolin-9-Yl]-N,N-Dimethylsulfamide

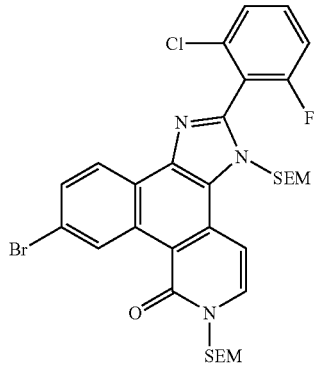

Step A: 9-bromo-2-(2-chloro-6-fluorophenyl)-3,6-bis{[2-(trimethylsilyl)ethoxy]methyl}-3,6-dihydro-7H-benzo[h]imidazo[4,5-f]isoquinolin-7-one The intermediate from Example 1 Step E (1.76 g, 3.99 mmol) was suspended in 150 mL THF and the flask was immersed in a room temperature water bath followed by the addition 11 mL (2.7 equiv) of a 1M solution of potassium tert-butoxide (in THF). After 45 minutes, 1.79 g of SEMCl (2.7 equiv) was added. The reaction was allowed to warm to ambient temperature overnight. The volatiles were removed in vacuo and the crude residue was dissolved in EtOAc and washed sequentially with a saturated solution of NaHCO$_3$ and brine. The solution was dried with MgSO$_4$ and filtered. Evaporation of the solvent under reduced pressure provided the crude residue that was purified on silica gel (gradient elution from 0 to 30% EtOAc/hexanes).

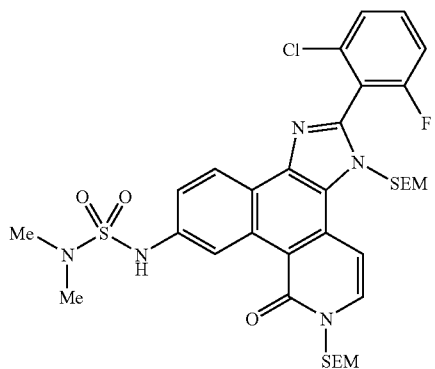

Step B: N'-(2-(2-chloro-6-fluorophenyl)-7-oxo-3,6-bis{[2-trimethylsilyl)ethoxy]methyl}-6,7-dihydro-3H-benzo[h]imidazo[4,5-f]isoquinolin-9-yl)-N,N-dimethylsulfamide The intermediate from Example 8 Step A (300 mg, 0.4240 mmol) was combined in a microwave vial with N,N-dimethylsulfamide (50 mg, 0.4027 mmol), Cs$_2$CO$_3$ (400 mg, 1.228 mmol), Pd$_2$(dba)$_3$ (20 mg, 0.0218 mmol), and Xantphos (36 mg, 0.0622 mmol). The vial was evacuated and purged with argon several times and the vial was sealed. Dioxane (10 mL) was added and the mixture was heated to 100° C. overnight. The reaction was cooled to ambient temperature and diluted with EtOAc and washed sequentially with a saturated solution of NaHCO$_3$ and brine. The solution was dried with MgSO$_4$ and filtered. Evaporation of the solvent under reduced pressure provided the crude residue that was purified on silica gel (gradient elution from 10 to 50% EtOAc/hexanes): [M+1]$^+$ 747.

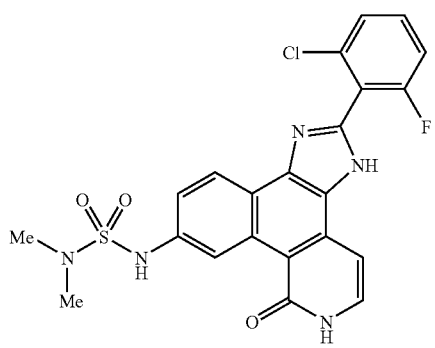

Step C: N'-[2-(2-chloro-6-fluorophenyl)-7-oxo-6,7-dihydro-3H-benzo[H]imidazo[4,5-f]isoquinolin-9-yl]-N,N-dimethylsulfamide The intermediate from Example 8 Step B (100 mg, 0.1340 mmol) was dissolved in 5 mL THF and treated with 5 equiv of a 1M solution of TBAF (in THF). The mixture was heated to 150° C. in a microwave for 15 minutes. The reaction was cooled to ambient temperature and diluted with EtOAc and washed sequentially with water and brine. The solution was dried with MgSO$_4$ and filtered. Evaporation of the solvent under reduced pressure provided the crude residue that was purified on silica gel (gradient elution from 0 to 100% EtOAc/hexanes): [M+1]$^+$ 486.

EXAMPLE 9

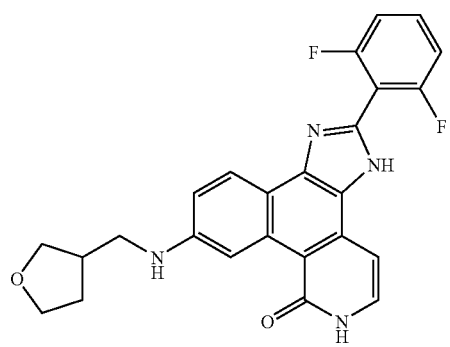

2-(2,6-Difluorophenyl)-9-[(Tetrahydrofuran-3-Ylmethyl)Amino]-3,6-Dihydro-7H-Benzo[H]Imidazo[4,5-F]Isoquinolin-7-One

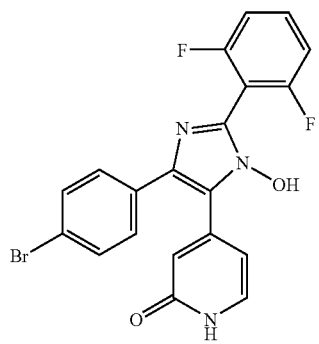

Step A: 4-[4-(4-bromophenyl)-2-(2,6-difluorophenyl)-1-hydroxy-1H-imidazol-5-yl]pyridin-2(1H)-one Using the general procedure found in Example 1 Step C, the intermediate from Example 1 Step B was combined with 2,6-difluorbenzaldehyde, ammonium acetate, and acetic acid: [M+1]$^+$ 444.

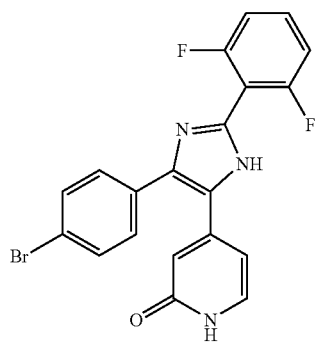

Step B: 4-[4-(4-bromophenyl)-2-(2,6-difluorophenyl)-1H-imidazol-5-yl]pyridin-2(1H)-one Using the general procedure in Example 1 Step D, the intermediate of Example 9 Step A was treated with TiCl₃ in methanol to provide the title compound: [M+1]⁺ 428.

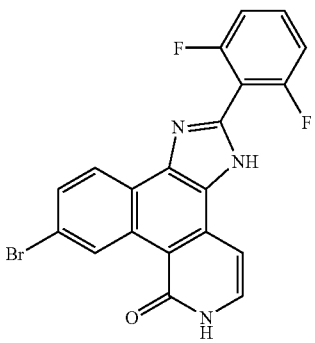

Step C: 9-bromo-2-(2,6-difluorophenyl)-3,6-dihydro-7H-benzo[h]imidazo[4,5-f]isoquinolin-7-one A solution of the intermediate in Example 9 Step B (12 g, 28 mmol) in THF (2 L) was stirred under irradiation of UV lamp for 30 h. The solvent was removed in vacuo. The crude residue was crystallized from methanol to afford the title compound. ¹H NMR (DMSO, 400 MHz) δ14.06 (s, 1H), 11.81 (s, 1H), 10.55 (s, 1H), 8.39 (d, J=8.6Hz, 1H), 7.81~7.89 (m, 1H), 7.58~7.72 (m, 2H), 7.19~7.40 (m, 3H): [M+1]⁺ 426.

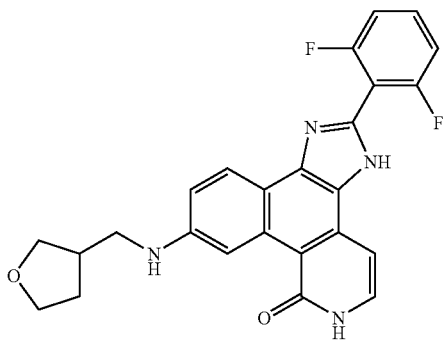

Step D: 2-(2,6-difluorophenyl)-9-[(tetrahydrofuran-3-ylmethyl)amino]-3,6-dihydro-7H-benzo[h]imidazo[4,5-f]isoquinolin-7-one A 0.5-2 mL microwave vial containing a stir bar was placed under argon by attaching a rubber septum and performing 4 vacuum/argon cycles. The intermediate from Example 9 Step C (100 mg, 0.146 mmol), sodium tert-butoxide (20.99 mg, 0.218 mmol), 2-(di-tert-butylphosphino)biphenyl (8.7 mg, 0.029 mmol), Pd₂(dba)₃ (13.33 mg, 0.015 mmol) were added, and the vial was sealed. While adding the solids to the vial, 30 mL of toluene was deoxygenated by bubbling argon through for 30 minutes; 1.0 mL of this was added to the sealed reaction vial. 3-(Aminomethyl)tetrahydrofuran (0.024 ml, 0.204 mmol) was added via microsyringe, and then argon was flushed gently through the vial for 5 min. The reaction was heated to 90° C. for 15 hours and then cooled to room temperature. A solution of tetrabutylammonium fluoride (1 Min tetrahydrofuran, 0.710 ml, 0.710 mmol) was added, and the vial was heated in a microwave oven for 10 min at 150° C. After cooling to room temperature, the reaction mixture was partitioned between a 1:1 mixture of EtOAc:ether (20 mL) and water (10 mL). The layers were separated, and the organic layer was washed sequentially with water (10 mL), saturated NaHCO₃ (10 mL), and brine (10 mL), dried over Na₂SO₄, filtered, and concentrated. The resulting solid was purified by reverse phase HPLC. After lyophilization, the title compound was obtained. ¹H NMR (600 MHz, DMSO) δ: 11.44 (s, 1 H), 9.57 (s, 1 H), 8.22 (m, 1 H), 7.68 (m, 1 H), 7.49 (t, 1 H, J=6.3 Hz), 7.38 (t, 2 H, J=8.2Hz), 7.16 (d, 2 H, J=5.6 Hz), 3.78 (m, 2 H), 3.64 (q, 1 H, J=7.6 Hz), 3.51 (dd, 1 H, J=8.5, 5.6 Hz), 3.17 (m, 2 H), 2.60 (m, 1 H), 2.04 (m, 1 H), 1.66 (m, 1 H): [M+1]⁺ 447.

EXAMPLE 10

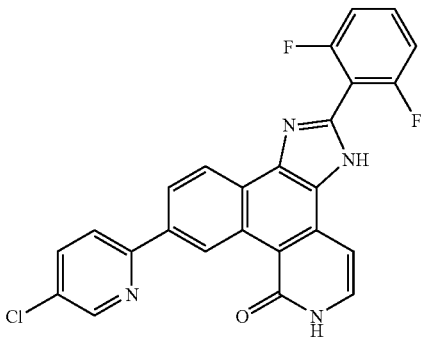

9-(5-Chloropyridin-2-Yl)-2-(2,6-Difluorophenyl)-3,6-Dihydro-7H-Benzo[H]Imidazo[4,5-F]Isoquinolin-7-One

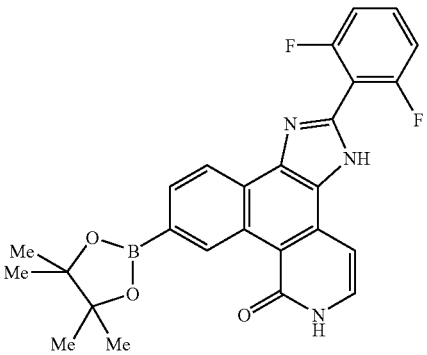

Step A: 2-(2,6-difluorophenyl)-9-(4,4,5,5-tetramethyl-1,3,2-dioxaborolan-2-yl)-3,6-dihydro-7H-benzo[h]imidazo[4,5-f]isoquinolin-7-one The intermediate from Example 9 Step C (250 mg, 0.59 mmol), Cy$_3$P (19.7 mg, 0.07 mmol), 4,4,4',4',5,5,5',5'-octamethyl-2,2,-bi-1,3,2-dioxaborolane (149 mg, 0.59 mmol), potassium acetate (144 mg, 1.47 mmol), and Pd$_2$(dba)$_3$ (26.9 mg, 0.03 mmol) were added to a sealed dry flask with stir bar. The flask was evacuated and back-filled with argon three times. Fully degassed dioxane (5.9 ml) was added. The flask was sealed and placed in an oil bath at 90° C. and stirred overnight. The mixture was filtered over a thin layer of celite, eluted with dichloromethane, partially rotovaped to remove some of the dichloromethane, and then triturated with hexanes. The precipitate was filtered to afford an off white solid. $^1$H NMR (600 MHz, CD$_3$OD) δ 10.72 (s, 1H); 8.33 (s, 1H); 8.03 (dd, 1H); 7.66 (m, 2H); 7.58 (m, 2H); 7.27 (m, 3H); 1.40 (s, 12H): [M+H]$^+$ 474.

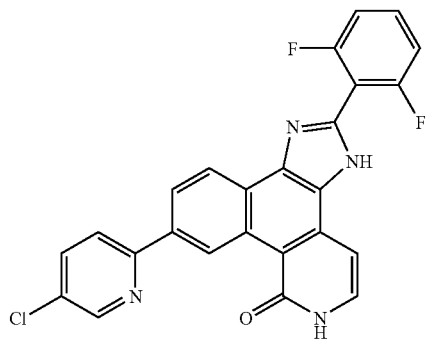

Step B: 9-(5-chloropyridin-2-yl)-2-(2,6-difluorophenyl)-3,6-dihydro-7H-benzo[h]imidazo[4,5-f]isoquinolin-7-one To a pressure flask with stir bar, the intermediate from Example 10 Step A (75mg, 0.16 mmol), 2-bromo-5-chloropyridine (33.5 mg, 0.17 mmol), and (Ph$_3$P)$_2$PdCl$_2$ (11.1 mg, 0.02 mmol) were added. The flask was purged of air and back-filled with argon (3×). Toluene (0.79 ml) and ethanol (0.79 ml) were bubbled with argon for at least 10 min before addition to the flask. Na$_2$CO$_3$ (0.24 ml, 0.48 mmol) was bubbled with argon, and then added to the flask. The mixture was heated at 90° C. in an oil bath overnight. Water was added to quench the reaction. The water layer was extracted with ethyl acetate 3×. The combined organics were washed with brine, dried with MgSO$_4$, filtered, and concentrated in vacuo. The crude compound was purified by reverse phase HPLC (10-100% acetonitrile in H$_2$O+0.05% TFA) to afford a light yellow solid. $^1$H NMR (600 MHz, CD$_3$OD) δ 14.00 (m, 1H); 11.40 (m, 1H); 10.97 (s, 1H); 8.73 (s, 1H); 8.53 (d, 1H); 8.29 (s, 1H); 8.05 (s, 2H); 7.56 (m, 3H); 7.25 (d, 2H): [M+H]$^+$ 459.

EXAMPLE 11

2-(2-Chloro-6-Fluorophenyl)-9-(2,6-Difluoropyridin-3-Yl)-3,6-Dihydro-7H-Benzo[H]Imidazo[4,5-F]Isoquinolin-7-One

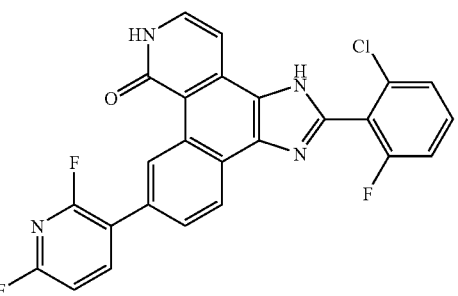

Step A: 2-(2-chloro-6-fluorophenyl)-9-(2,6-difluoropyridin-3-yl)-3,6-dihydro-7H-benzo[h]imidazo[4,5-f]isoquinolin-7-one A sealed tube was charged with the intermediate from Example 1 Step E (230 mg, 0.52 mmol), (2,6-difluoropyridin-3-yl)boronic acid (580 mg, 3.6 mmol), and bis(triphenylphosphine)palladium(n) chloride (73 mg, 0.1 mmol). The tube was evacuated and backfilled with argon three times. Fully degassed toluene (3.0 mL) and ethanol (3.0 mL) were added, followed by the addition of 2.0M aqueous sodium carbonate solution (2.6 mL, 5.2 mmol). The tube was sealed, placed in an oil bath at 90° C., and stirred for 3 hours. The reaction mixture was then cooled and poured into a mixture of ethyl acetate and brine. The aqueous layer was extracted twice with ethyl acetate and the combined organics were dried over magnesium sulfate, filtered, concentrated in vacuo. Purification via flash chromatography (silica, 0-20% methanol/dichloromethane) was followed by purification via preparative chiral HPLC (AD column, 25% ethanol/heptane isocratic) to afford the title compound. $^1$H NMR (600 MHz, d6-DMSO) δ 11.75 (s, 1H), 10.57 (s, 1H), 8.49 (broad s, 1H), 8.43 (q, 1H), 7.92 (d, 1H), 7.72-7.69 (m, 1H), 7.62-7.61 (m, 2H), 7.58-7.52 (m, 1H), 7.37 (dd, 1H), 7.27 (broad s, 1H). Imidazole proton was not observed [M+H]$^+$ 476. τ$_R$: 9.44 min (analytical chiral HPLC, AD column, 0.46 cm×25 cm, 25% ethanol/heptane, isocratic, flow rate=0.75 mL/min).

Additional analogues were prepared using procedures similar to those described in the above examples.

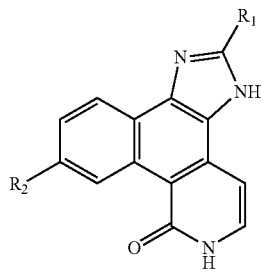

| Compound Name | R1 | R2 | M + 1 |
|---|---|---|---|
| 9-bromo-2-(2-chlorophenyl)-3,6-dihydro-7H-benzo[h]imidazo[4,5-f]isoquinolin-7-one | 2-chlorophenyl | Br | 425 |
| 9-bromo-2-(tetrahydro-2H-pyran-4-yl)-3,6-dihydro-7H-benzo[h]imidazo[4,5-f]isoquinolin-7-one | tetrahydro-2H-pyran-4-yl | Br | 398 |
| 9-bromo-2-(tetrahydrofuran-3-yl)-3,6-dihydro-7H-benzo[h]imidazo[4,5-f]isoquinolin-7-one | tetrahydrofuran-3-yl | Br | 384 |
| 9-bromo-2-(tetrahydro-2H-pyran-3-yl)-3,6-dihydro-7H-benzo[h]imidazo[4,5-f]isoquinolin-7-one | tetrahydro-2H-pyran-3-yl | Br | 398 |
| 9-bromo-2-(2,2-dimethyltetrahydro-2H-pyran-4-yl)-3,6-dihydro-7H-benzo[h]imidazo[4,5-f]isoquinolin-7-one | 2,2-dimethyltetrahydro-2H-pyran-4-yl | Br | 426 |
| 9-bromo-2-(1-isopropyl-1H-pyrazol-4-yl)-3,6-dihydro-7H-benzo[h]imidazo[4,5-f]isoquinolin-7-one | 1-isopropyl-1H-pyrazol-4-yl | Br | 422 |
| 9-bromo-2-pyridin-3-yl-3,6-dihydro-7H-benzo[h]imidazo[4,5-f]isoquinolin-7-one | pyridin-3-yl | Br | 391 |
| 9-bromo-2-(1,5-dimethyl-1H-pyrazol-4-yl)-3,6-dihydro-7H-benzo[h]imidazo[4,5-f]isoquinolin-7-one | 1,5-dimethyl-1H-pyrazol-4-yl | Br | 408 |
| 9-bromo-2-isoquinolin-8-yl-3,6-dihydro-7H-benzo[h]imidazo[4,5-f]isoquinolin-7-one | isoquinolin-8-yl | Br | 441 |

-continued

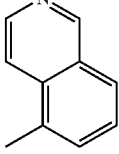

| Compound Name | R1 | R2 | M + 1 |
|---|---|---|---|
| 9-bromo-2-isoquinolin-5-yl-3,6-dihydro-7H-benzo[h]imidazo[4,5-f]isoquinolin-7-one | 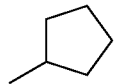 | Br | 441 |
| 9-bromo-2-cyclopentyl-3,6-dihydro-7H-benzo[h]imidazo[4,5-f]isoquinolin-7-one | 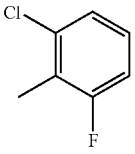 | Br | 382 |
| 9-bromo-2-(2-chloro-6-fluorophenyl)-3,6-dihydro-7H-benzo[h]imidazo[4,5-f]isoquinolin-7-one | 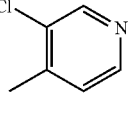 | Br | 442 |
| 9-bromo-2-(3-chloropyridin-4-yl)-3,6-dihydro-7H-benzo[h]imidazo[4,5-f]isoquinolin-7-one | 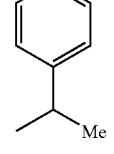 | Br | 365 |
| 9-bromo-2-(1-phenylethyl)-3,6-dihydro-7H-benzo[h]imidazo[4,5-f]isoquinolin-7-one | 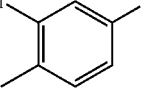 | Br | 418 |
| 9-bromo-2-(2-chloro-4-fluorophenyl)-3,6-dihydro-7H-benzo[h]imidazo[4,5-f]isoquinolin-7-one | 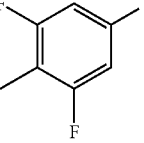 | Br | 442 |
| 9-bromo-2-(2,4,6-trifluorophenyl)-3,6-dihydro-7H-benzo[h]imidazo[4,5-f]isoquinolin-7-one | 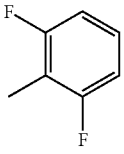 | Br | 444 |
| 9-bromo-2-(2,6-difluorophenyl)-3,6-dihydro-7H-benzo[h]imidazo[4,5-f]isoquinolin-7-one | 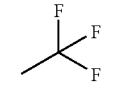 | Br | 426 |
| 9-bromo-2-(trifluoromethyl)-3,6-dihydro-7H-benzo[h]imidazo[4,5-f]isoquinolin-7-one | F₃C- | Br | 382 |

-continued

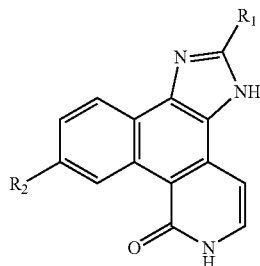

| Compound Name | R1 | R2 | M + 1 |
|---|---|---|---|
| 2-cyclopentyl-9-(isobutylamino)-3,6-dihydro-7H-benzo[h]imidazo[4,5-f]isoquinolin-7-one | cyclopentyl | Me-CH(Me)-NH- | 375 |
| 2-cyclopentyl-9-{[(1,5-dimethyl-1H-pyrazol-3-yl)methyl]amino}-3,6-dihydro-7H-benzo[h]imidazo[4,5-f]isoquinolin-7-one | cyclopentyl | 1,5-dimethyl-1H-pyrazol-3-yl-NH- | 427 |
| 9-{[1-(4-chlorophenyl)ethyl]amino}-2-cyclopentyl-3,6-dihydro-7H-benzo[h]imidazo[4,5-f]isoquinolin-7-one | cyclopentyl | 1-(4-chlorophenyl)ethyl-NH- | 456 |
| 2-cyclopentyl-9-[(tetrahydrofuran-2-ylmethyl)amino]-3,6-dihydro-7H-benzo[h]imidazo[4,5-f]isoquinolin-7-one | cyclopentyl | tetrahydrofuran-2-ylmethyl-NH- | 403 |
| 2-cyclopentyl-9-[(2-methoxyethyl)amino]-3,6-dihydro-7H-benzo[h]imidazo[4,5-f]isoquinolin-7-one | cyclopentyl | MeO-CH2CH2-NH- | 377 |
| 2-cyclopentyl-9-[(2-hydroxy-2-phenylethyl)(methyl)amino]-3,6-dihydro-7H-benzo[h]imidazo[4,5-f]isoquinolin-7-one | cyclopentyl | Ph-CH(OH)-CH2-N(Me)- | 453 |
| 2-cyclopentyl-9-[(2R)-2-phenylmorpholin-4-yl]-3,6-dihydro-7H-benzo[h]imidazo[4,5-f]isoquinolin-7-one | cyclopentyl | (2R)-2-phenylmorpholin-4-yl | 465 |
| 2-cyclopentyl-9-[(3R)-3-methoxypyrrolidin-1-yl]-3,6-dihydro-7H-benzo[h]imidazo[4,5-f]isoquinolin-7-one | cyclopentyl | (3R)-3-methoxypyrrolidin-1-yl | 403 |

-continued

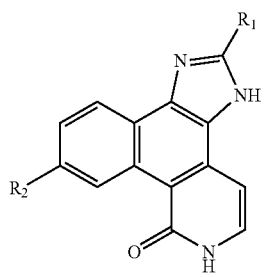

| Compound Name | R1 | R2 | M + 1 |
|---|---|---|---|
| 2-(2,6-difluorophenyl)-9-[(tetrahydrofuran-2-ylmethyl)amino]-3,6-dihydro-7H-benzo[h]imidazo[4,5-f]isoquinolin-7-one | 2,6-difluorophenyl | (tetrahydrofuran-2-yl)methylamino | 447 |
| N'-[2-(2-chloro-6-fluorophenyl)-7-oxo-6,7-dihydro-1H-benzo[h]imidazo[4,5-f]isoquinolin-9-yl]-N,N-dimethylsulfamide | 2-chloro-6-fluorophenyl | Me-N(Me)-S(O)₂-NH-Me | 486 |
| 2-(2,6-difluorophenyl)-9-{[(3-methyloxetan-3-yl)methyl]amino}-3,6-dihydro-7H-benzo[h]imidazo[4,5-f]isoquinolin-7-one | 2,6-difluorophenyl | (3-methyloxetan-3-yl)methylamino | 447 |
| 2-(2,6-difluorophenyl)-9-[(tetrahydrofuran-3-ylmethyl)amino]-3,6-dihydro-7H-benzo[h]imidazo[4,5-f]isoquinolin-7-one | 2,6-difluorophenyl | (tetrahydrofuran-3-yl)methylamino | 447 |
| 2-(2,6-difluorophenyl)-9-{[(2-methyltetrahydrofuran-2-yl)methyl]amino}-3,6-dihydro-7H-benzo[h]imidazo[4,5-f]isoquinolin-7-one | 2,6-difluorophenyl | (2-methyltetrahydrofuran-2-yl)methylamino | 461 |
| 2-(2,6-difluorophenyl)-9-[(1,4-dioxan-2-ylmethyl)amino]-3,6-dihydro-7H-benzo[h]imidazo[4,5-f]isoquinolin-7-one | 2,6-difluorophenyl | (1,4-dioxan-2-yl)methylamino | 463 |
| 3-{[2-(2,6-difluorophenyl)-7-oxo-6,7-dihydro-3H-benzo[h]imidazo[4,5-f]isoquinolin-9-yl]amino}propanenitrile | 2,6-difluorophenyl | NC-CH₂CH₂-NH | 416 |
| 2-(2,6-difluorophenyl)-9-{[2-(1H-imidazol-4-yl)ethyl]amino}-3,6-dihydro-7H-benzo[h]imidazo[4,5-f]isoquinolin-7-one | 2,6-difluorophenyl | 2-(1H-imidazol-4-yl)ethylamino | 457 |

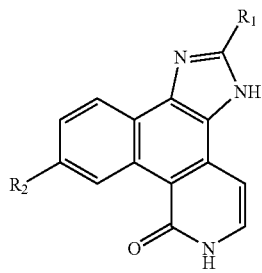

| Compound Name | R1 | R2 | M + 1 |
|---|---|---|---|
| 9-[(2,4-difluorobenzyl)amino]-2-(2,6-difluorophenyl)-3,6-dihydro-7H-benzo[h]imidazo[4,5-f]isoquinolin-7-one | 2,6-difluorophenyl | (2,4-difluorobenzyl)amino | 489 |
| 2-(2,6-difluorophenyl)-9-{[2-(pyridin-2-ylamino)ethyl]amino}-3,6-dihydro-7H-benzo[h]imidazo[4,5-f]isoquinolin-7-one | 2,6-difluorophenyl | [2-(pyridin-2-ylamino)ethyl]amino | 483 |
| 2-(2,6-difluorophenyl)-9-[(2,3-dihydroxypropyl)amino]-3,6-dihydro-7H-benzo[h]imidazo[4,5-f]isoquinolin-7-one | 2,6-difluorophenyl | (2,3-dihydroxypropyl)amino | 437 |
| 2-(2-chlorophenyl)-9-(1-methyl-1H-pyrazol-4-yl)-3,6-dihydro-7H-benzo[h]imidazo[4,5-f]isoquinolin-7-one | 2-chlorophenyl | 1-methyl-1H-pyrazol-4-yl | 426 |
| 2-(2-chlorophenyl)-9-pyridin-4-yl-3,6-dihydro-7H-benzo[h]imidazo[4,5-f]isoquinolin-7-one | 2-chlorophenyl | pyridin-4-yl | 423 |
| tert-butyl 4-{4-[2-(2-chlorophenyl)-7-oxo-6,7-dihydro-3H-benzo[h]imidazo[4,5-f]isoquinolin-9-yl]phenyl}piperazine-1-carboxylate | 2-chlorophenyl | 4-(4-BOC-piperazin-1-yl)phenyl | 606 |
| 2-(2-chlorophenyl)-9-(4-piperazin-1-ylphenyl)-3,6-dihydro-7H-benzo[h]imidazo[4,5-f]isoquinolin-7-one | 2-chlorophenyl | 4-(piperazin-1-yl)phenyl | |
| 2-(2-chlorophenyl)-9-[3-(dimethylamino)phenyl]-3,6-dihydro-7H-benzo[h]imidazo[4,5-f]isoquinolin-7-one | 2-chlorophenyl | 3-(dimethylamino)phenyl | 465 |

-continued

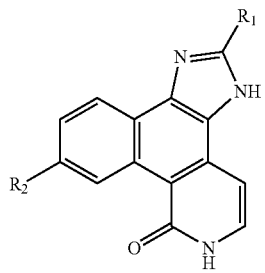

| Compound Name | R1 | R2 | M + 1 |
|---|---|---|---|
| 9-biphenyl-3-yl-2-(2-chlorophenyl)-3,6-dihydro-7H-benzo[h]imidazo[4,5-f]isoquinolin-7-one | 2-chlorophenyl | biphenyl-3-yl | 499 |
| 9-biphenyl-2-yl-2-(2-chlorophenyl)-3,6-dihydro-7H-benzo[h]imidazo[4,5-f]isoquinolin-7-one | 2-chlorophenyl | biphenyl-2-yl | 499 |
| 2-(2-chlorophenyl)-9-pyridin-3-yl-3,6-dihydro-7H-benzo[h]imidazo[4,5-f]isoquinolin-7-one | 2-chlorophenyl | pyridin-3-yl | 423 |
| 4-[2-(2-chlorophenyl)-7-oxo-6,7-dihydro-3H-benzo[h]imidazo[4,5-f]isoquinolin-9-yl]-N,N-dimethylbenzamide | 2-chlorophenyl | 4-(N,N-dimethylcarbamoyl)phenyl | 493 |
| 4-[2-(2-chlorophenyl)-7-oxo-6,7-dihydro-3H-benzo[h]imidazo[4,5-f]isoquinolin-9-yl]-N-[2-(dimethylamino)ethyl]benzamide | 2-chlorophenyl | 4-{[2-(dimethylamino)ethyl]carbamoyl}phenyl | 536 |
| 2-(2-chlorophenyl)-9-{4-[(4-methylpiperazin-1-yl)carbonyl]phenyl}-3,6-dihydro-7H-benzo[h]imidazo[4,5-f]isoquinolin-7-one | 2-chlorophenyl | 4-[(4-methylpiperazin-1-yl)carbonyl]phenyl | 548 |

-continued

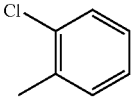

| Compound Name | R1 | R2 | M + 1 |
|---|---|---|---|
| 2-(2-chlorophenyl)-9-[2-(4-methylpiperazin-1-yl)pyridin-4-yl]-3,6-dihydro-7H-benzo[h]imidazo[4,5-f]isoquinolin-7-one | 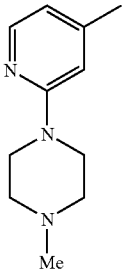 | 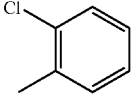 | 521 |
| 2-(2-chlorophenyl)-9-[4-(morpholin-4-ylcarbonyl)phenyl]-3,6-dihydro-7H-benzo[h]imidazo[4,5-f]isoquinolin-7-one | 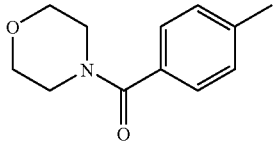 | 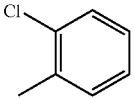 | 535 |
| N-{3-[2-(2-chlorophenyl)-7-oxo-6,7-dihydro-3H-benzo[h]imidazo[4,5-f]isoquinolin-9-yl]phenyl}methanesulfonamide | 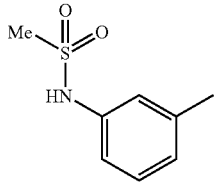 | 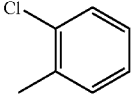 | 515 |
| N-{4-[2-(2-chlorophenyl)-7-oxo-6,7-dihydro-3H-benzo[h]imidazo[4,5-f]isoquinolin-9-yl]phenyl}methanesulfonamide | 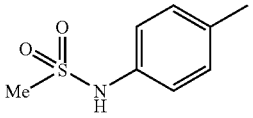 | 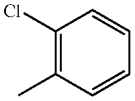 | 515 |
| 2-(2-chlorophenyl)-9-(4-methoxyphenyl)-3,6-dihydro-7H-benzo[h]imidazo[4,5-f]isoquinolin-7-one | 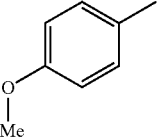 | 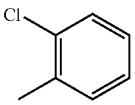 | 452 |
| 2-(2-chlorophenyl)-9-(3-methoxyphenyl)-3,6-dihydro-7H-benzo[h]imidazo[4,5-f]isoquinolin-7-one | 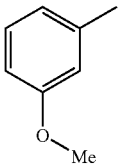 | 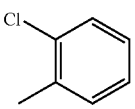 | 452 |
| 2-(2-chlorophenyl)-9-(2-methoxyphenyl)-3,6-dihydro-7H-benzo[h]imidazo[4,5-f]isoquinolin-7-one | | 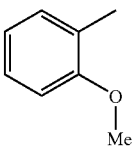 | 452 |

-continued

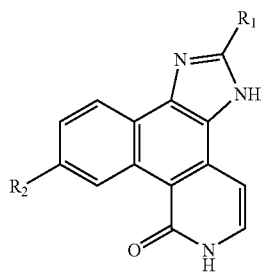

| Compound Name | R1 | R2 | M + 1 |
|---|---|---|---|
| 4-[2-(2-chlorophenyl)-7-oxo-6,7-dihydro-3H-benzo[h]imidazo[4,5-f]isoquinolin-9-yl]-N-ethylbenzamide | 2-chlorophenyl | 4-methyl-N-ethylbenzamide | 493 |
| 4-[2-(2-chlorophenyl)-7-oxo-6,7-dihydro-3H-benzo[h]imidazo[4,5-f]isoquinolin-9-yl]-N-isobutylbenzamide | 2-chlorophenyl | 4-methyl-N-isobutylbenzamide | 521 |
| 2-(2-chlorophenyl)-9-quinolin-5-yl-3,6-dihydro-7H-benzo[h]imidazo[4,5-f]isoquinolin-7-one | 2-chlorophenyl | quinolin-5-yl | 473 |
| 2-(2-chlorophenyl)-9-(1H-pyrazol-3-yl)-3,6-dihydro-7H-benzo[h]imidazo[4,5-f]isoquinolin-7-one | 2-chlorophenyl | 1H-pyrazol-3-yl | 412 |
| 2-(2-chlorophenyl)-9-[6-(4-methylpiperazin-1-yl)pyridin-3-yl]-3,6-dihydro-7H-benzo[h]imidazo[4,5-f]isoquinolin-7-one | 2-chlorophenyl | 6-(4-methylpiperazin-1-yl)pyridin-3-yl | 521 |
| 2-cyclopentyl-9-(1H-pyrazol-3-yl)-3,6-dihydro-7H-benzo[h]imidazo[4,5-f]isoquinolin-7-one | cyclopentyl | 1H-pyrazol-3-yl | 370 |
| 2-(2-chloro-6-fluorophenyl)-9-[4-(morpholin-4-ylcarbonyl)phenyl]-3,6-dihydro-7H-benzo[h]imidazo[4,5-f]isoquinolin-7-one | 2-chloro-6-fluorophenyl | 4-(morpholin-4-ylcarbonyl)phenyl | 553 |
| 9-(1H-pyrazol-3-yl)-2-(tetrahydrofuran-3-yl)-3,6-dihydro-7H-benzo[h]imidazo[4,5-f]isoquinolin-7-one | tetrahydrofuran-3-yl | 1H-pyrazol-3-yl | 372 |

-continued

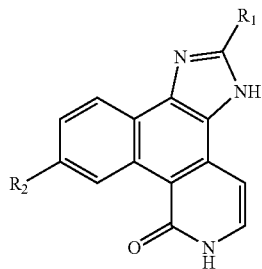

| Compound Name | R1 | R2 | M + 1 |
|---|---|---|---|
| 2-cyclopentyl-N-[2-(dimethylamino)ethyl]-7-oxo-6,7-dihydro-3H-benzo[h]imidazo[4,5-f]isoquinoline-9-carboxamide | cyclopentyl | Me₂N-CH₂CH₂-NH-C(O)- | 418 |
| 2-cyclopentyl-N-(3-methylbutyl)-7-oxo-6,7-dihydro-3H-benzo[h]imidazo[4,5-f]isoquinoline-9-carboxamide | cyclopentyl | Me₂CH-CH₂-CH₂-NH-C(O)- | 417 |
| 2-cyclopentyl-9-[(4-methylpiperazin-1-yl)carbonyl]-3,6-dihydro-7H-benzo[h]imidazo[4,5-f]isoquinolin-7-one | cyclopentyl | 4-methylpiperazin-1-yl-C(O)- | 430 |
| 2-cyclopentyl-9-(morpholin-4-ylcarbonyl)-3,6-dihydro-7H-benzo[h]imidazo[4,5-f]isoquinolin-7-one | cyclopentyl | morpholin-4-yl-C(O)- | 417 |
| 2-cyclopentyl-9-[(4-hydroxypiperidin-1-yl)carbonyl]-3,6-dihydro-7H-benzo[h]imidazo[4,5-f]isoquinolin-7-one | cyclopentyl | 4-hydroxypiperidin-1-yl-C(O)- | 431 |
| 2-cyclopentyl-9-(piperidin-1-ylcarbonyl)-3,6-dihydro-7H-benzo[h]imidazo[4,5-f]isoquinolin-7-one | cyclopentyl | piperidin-1-yl-C(O)- | 415 |
| 2-cyclopentyl-7-oxo-N-(pyridin-2-ylmethyl)-6,7-dihydro-3H-benzo[h]imidazo[4,5-f]isoquinoline-9-carboxamide | cyclopentyl | pyridin-2-yl-CH₂-NH-C(O)- | 438 |

-continued

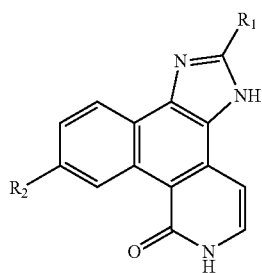

| Compound Name | R1 | R2 | M + 1 |
| --- | --- | --- | --- |
| 2-cyclopentyl-7-oxo-N-(pyridin-3-ylmethyl)-6,7-dihydro-3H-benzo[h]imidazo[4,5-f]isoquinoline-9-carboxamide | cyclopentyl | pyridin-3-ylmethyl carboxamide | 438 |
| 2-cyclopentyl-N-(methylsulfonyl)-7-oxo-6,7-dihydro-3H-benzo[h]imidazo[4,5-f]isoquinoline-9-carboxamide | cyclopentyl | methylsulfonyl carboxamide | 425 |
| N-benzyl-2-cyclopentyl-7-oxo-6,7-dihydro-3H-benzo[h]imidazo[4,5-f]isoquinoline-9-carboxamide | cyclopentyl | benzyl carboxamide | 437 |
| 9-(1H-pyrazol-3-yl)-2-(tetrahydrofuran-3-yl)-3,6-dihydro-7H-benzo[h]imidazo[4,5-f]isoquinolin-7-one | tetrahydrofuran-3-yl | 1H-pyrazol-3-yl | 372 |
| 2-cyclopentyl-9-(6-methoxypyridin-3-yl)-3,6-dihydro-7H-benzo[h]imidazo[4,5-f]isoquinolin-7-one | cyclopentyl | 6-methoxypyridin-3-yl | 411 |
| 2-cyclopentyl-9-(1H-pyrazol-4-yl)-3,6-dihydro-7H-benzo[h]imidazo[4,5-f]isoquinolin-7-one | cyclopentyl | 1H-pyrazol-4-yl | 370 |
| 2-cyclopentyl-9-(2,6-dimethoxypyridin-3-yl)-3,6-dihydro-7H-benzo[h]imidazo[4,5-f]isoquinolin-7-one | cyclopentyl | 2,6-dimethoxypyridin-3-yl | 441 |
| 2-cyclopentyl-9-pyrimidin-5-yl-3,6-dihydro-7H-benzo[h]imidazo[4,5-f]isoquinolin-7-one | cyclopentyl | pyrimidin-5-yl | 382 |

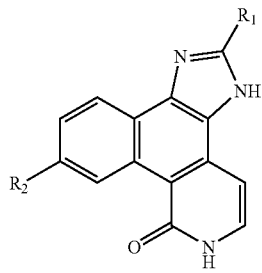

| Compound Name | R1 | R2 | M + 1 |
|---|---|---|---|
| 2-cyclopentyl-9-(3,5-dimethylisoxazol-4-yl)-3,6-dihydro-7H-benzo[h]imidazo[4,5-f]isoquinolin-7-one | cyclopentyl | 3,5-dimethylisoxazol-4-yl | 399 |
| 2-(2-chloro-6-fluorophenyl)-9-(1H-pyrazol-3-yl)-1,6-dihydro-7H-benzo[h]imidazo[4,5-f]isoquinolin-7-one | 2-chloro-6-fluorophenyl | 1H-pyrazol-3-yl | 430 |
| 2-(2-chloro-6-fluorophenyl)-9-(1H-pyrazol-4-yl)-3,6-dihydro-7H-benzo[h]imidazo[4,5-f]isoquinolin-7-one | 2-chloro-6-fluorophenyl | 1H-pyrazol-4-yl | 430 |
| 2-(2-chloro-6-fluorophenyl)-9-pyridin-3-yl-1,6-dihydro-7H-benzo[h]imidazo[4,5-f]isoquinolin-7-one | 2-chloro-6-fluorophenyl | pyridin-3-yl | 441 |
| 2-(2-chloro-6-fluorophenyl)-9-(4-morpholin-4-ylphenyl)-3,6-dihydro-7H-benzo[h]imidazo[4,5-f]isoquinolin-7-one | 2-chloro-6-fluorophenyl | 4-morpholin-4-ylphenyl | 525 |
| 2-(2-chloro-6-fluorophenyl)-9-(2-morpholin-4-ylpyridin-4-yl)-3,6-dihydro-7H-benzo[h]imidazo[4,5-f]isoquinolin-7-one | 2-chloro-6-fluorophenyl | 2-morpholin-4-ylpyridin-4-yl | 526 |
| 2-(2-chloro-6-fluorophenyl)-9-pyridin-4-yl-3,6-dihydro-7H-benzo[h]imidazo[4,5-f]isoquinolin-7-one | 2-chloro-6-fluorophenyl | pyridin-4-yl | 441 |

-continued

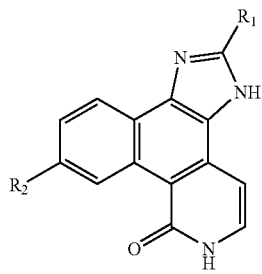

| Compound Name | R1 | R2 | M + 1 |
|---|---|---|---|
| 9-(6-aminopyridin-3-yl)-2-(2-chloro-6-fluorophenyl)-3,6-dihydro-7H-benzo[h]imidazo[4,5-f]isoquinolin-7-one | 2-chloro-6-fluorophenyl | 6-aminopyridin-3-yl | 456 |
| 2-(2-chloro-6-fluorophenyl)-9-(6-methoxypyridin-3-yl)-3,6-dihydro-7H-benzo[h]imidazo[4,5-f]isoquinolin-7-one | 2-chloro-6-fluorophenyl | 6-methoxypyridin-3-yl | 471 |
| 2-(2-chloro-6-fluorophenyl)-9-(4-methoxypyridin-3-yl)-3,6-dihydro-7H-benzo[h]imidazo[4,5-f]isoquinolin-7-one | 2-chloro-6-fluorophenyl | 4-methoxypyridin-3-yl | 471 |
| 2-(2-chloro-6-fluorophenyl)-9-{6-[(2-morpholin-4-ylethyl)amino]pyridin-3-yl}-3,6-dihydro-7H-benzo[h]imidazo[4,5-f]isoquinolin-7-one | 2-chloro-6-fluorophenyl | 6-[(2-morpholin-4-ylethyl)amino]pyridin-3-yl | 469 |
| 2-(2-chloro-6-fluorophenyl)-9-(6-hydroxypyridin-3-yl)-3,6-dihydro-7H-benzo[h]imidazo[4,5-f]isoquinolin-7-one | 2-chloro-6-fluorophenyl | 6-hydroxypyridin-3-yl | 457 |
| 2-(2-chloro-6-fluorophenyl)-9-(5-chloro-2-methoxypyridin-4-yl)-3,6-dihydro-7H-benzo[h]imidazo[4,5-f]isoquinolin-7-one | 2-chloro-6-fluorophenyl | 5-chloro-2-methoxypyridin-4-yl | 505 |
| 2-(2-chloro-6-fluorophenyl)-9-(6-chloropyridin-3-yl)-3,6-dihydro-7H-benzo[h]imidazo[4,5-f]isoquinolin-7-one | 2-chloro-6-fluorophenyl | 6-chloropyridin-3-yl | 475 |

-continued

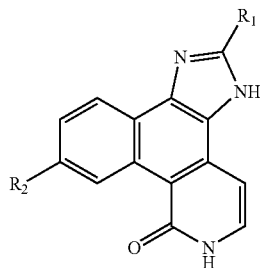

| Compound Name | R1 | R2 | M + 1 |
|---|---|---|---|
| N-{3-[2-(2-chloro-6-fluorophenyl)-7-oxo-6,7-dihydro-3H-benzo[h]imidazo[4,5-f]isoquinolin-9-yl]pyridin-2-yl}-2,2-dimethylpropanamide | 2-chloro-6-fluorophenyl | 3-methyl-N-(2-methylpropan-2-yl)pyridine-2-carboxamide | 540 |
| 2-(2-chloro-6-fluorophenyl)-9-[2-(cyclopropylmethoxy)pyridin-3-yl]-3,6-dihydro-7H-benzo[h]imidazo[4,5-f]isoquinolin-7-one | 2-chloro-6-fluorophenyl | 2-(cyclopropylmethoxy)-3-methylpyridine | 511 |
| 2-(2-chloro-6-fluorophenyl)-9-(6-fluoropyridin-3-yl)-3,6-dihydro-7H-benzo[h]imidazo[4,5-f]isoquinolin-7-one | 2-chloro-6-fluorophenyl | 2-fluoro-5-methylpyridine | 459 |
| 5-[2-(2-chloro-6-fluorophenyl)-7-oxo-6,7-dihydro-3H-benzo[h]imidazo[4,5-f]isoquinolin-9-yl]pyridine-2-carbonitrile | 2-chloro-6-fluorophenyl | 5-methylpyridine-2-carbonitrile | 466 |
| 2-(2-chloro-6-fluorophenyl)-9-(2,6-difluoropyridin-3-yl)-3,6-dihydro-7H-benzo[h]imidazo[4,5-f]isoquinolin-7-one | 2-chloro-6-fluorophenyl | 2,6-difluoro-3-methylpyridine | 477 |
| 2-(2-chloro-6-fluorophenyl)-9-(6-methylpyridin-3-yl)-3,6-dihydro-7H-benzo[h]imidazo[4,5-f]isoquinolin-7-one | 2-chloro-6-fluorophenyl | 2,5-dimethylpyridine | 455 |
| 2-(2-chloro-6-fluorophenyl)-9-pyrimidin-5-yl-3,6-dihydro-7H-benzo[h]imidazo[4,5-f]isoquinolin-7-one | 2-chloro-6-fluorophenyl | 5-methylpyrimidine | 442 |

-continued

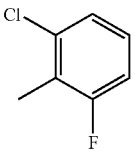

| Compound Name | R1 | R2 | M + 1 |
|---|---|---|---|
| 2-(2-chloro-6-fluorophenyl)-9-quinolin-3-yl-3,6-dihydro-7H-benzo[h]imidazo[4,5-f]isoquinolin-7-one | 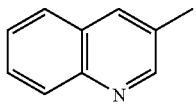 | 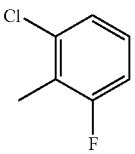 | 491 |
| 2-(2-chloro-6-fluorophenyl)-9-[6-(dimethylamino)pyridin-3-yl]-3,6-dihydro-7H-benzo[h]imidazo[4,5-f]isoquinolin-7-one | 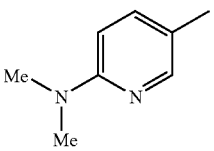 | 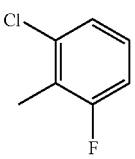 | 484 |
| 2-(2-chloro-6-fluorophenyl)-9-(3-furyl)-3,6-dihydro-7H-benzo[h]imidazo[4,5-f]isoquinolin-7-one | 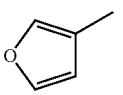 | 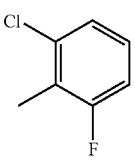 | 430 |
| 2-(2-chloro-6-fluorophenyl)-9-(1-methyl-1H-pyrazol-4-yl)-3,6-dihydro-7H-benzo[h]imidazo[4,5-f]isoquinolin-7-one | 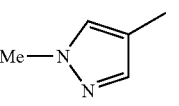 | 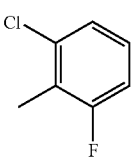 | 444 |
| 9-(4-aminophenyl)-2-(2-chloro-6-fluorophenyl)-3,6-dihydro-7H-benzo[h]imidazo[4,5-f]isoquinolin-7-one | 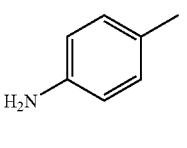 | 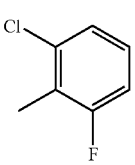 | 455 |
| 9-(3-aminophenyl)-2-(2-chloro-6-fluorophenyl)-3,6-dihydro-7H-benzo[h]imidazo[4,5-f]isoquinolin-7-one | 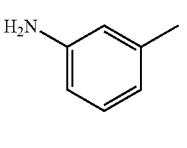 | 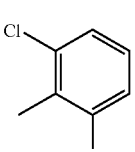 | 455 |
| 2-(2-chloro-6-fluorophenyl)-9-[4-(dimethylamino)phenyl]-3,6-dihydro-7H-benzo[h]imidazo[4,5-f]isoquinolin-7-one | 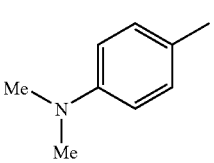 | 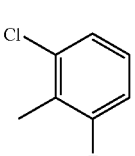 | 483 |
| 2-(2-chloro-6-fluorophenyl)-9-{2-[(dimethylamino)methyl]phenyl}-3,6-dihydro-7H-benzo[h]imidazo[4,5-f]isoquinolin-7-one | 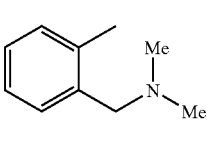 | | 497 |

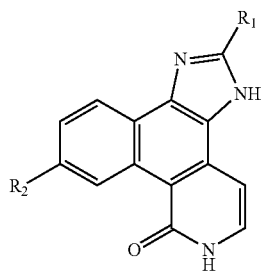

| Compound Name | R1 | R2 | M + 1 |
|---|---|---|---|
| 2-(2-chloro-6-fluorophenyl)-9-(2,6-dimethoxypyridin-3-yl)-3,6-dihydro-7H-benzo[h]imidazo[4,5-f]isoquinolin-7-one | 2-chloro-6-fluorophenyl | 2,6-dimethoxypyridin-3-yl | 501 |
| 2-(2-chloro-6-fluorophenyl)-9-(3,5-dimethyl-1H-pyrazol-4-yl)-3,6-dihydro-7H-benzo[h]imidazo[4,5-f]isoquinolin-7-one | 2-chloro-6-fluorophenyl | 3,5-dimethyl-1H-pyrazol-4-yl | 458 |
| 2-(2-chloro-6-fluorophenyl)-9-(1,3,5-trimethyl-1H-pyrazol-4-yl)-3,6-dihydro-7H-benzo[h]imidazo[4,5-f]isoquinolin-7-one | 2-chloro-6-fluorophenyl | 1,3,5-trimethyl-1H-pyrazol-4-yl | 472 |
| 2-(2-chloro-6-fluorophenyl)-9-isoquinolin-4-yl-3,6-dihydro-7H-benzo[h]imidazo[4,5-f]isoquinolin-7-one | 2-chloro-6-fluorophenyl | isoquinolin-4-yl | 491 |
| 2-(2-chloro-6-fluorophenyl)-9-(2-methoxypyrimidin-5-yl)-3,6-dihydro-7H-benzo[h]imidazo[4,5-f]isoquinolin-7-one | 2-chloro-6-fluorophenyl | 2-methoxypyrimidin-5-yl | 472 |
| 2-(2-chloro-6-fluorophenyl)-9-(6-morpholin-4-ylpyridin-3-yl)-3,6-dihydro-7H-benzo[h]imidazo[4,5-f]isoquinolin-7-one | 2-chloro-6-fluorophenyl | 6-morpholin-4-ylpyridin-3-yl | 526 |
| 2-(2-chloro-6-fluorophenyl)-9-(2-methoxypyridin-3-yl)-3,6-dihydro-7H-benzo[h]imidazo[4,5-f]isoquinolin-7-one | 2-chloro-6-fluorophenyl | 2-methoxypyridin-3-yl | 471 |

-continued

| Compound Name | R1 | R2 | M + 1 |
|---|---|---|---|
| 2-(2-chloro-6-fluorophenyl)-9-(2-fluoroquinolin-3-yl)-3,6-dihydro-7H-benzo[h]imidazo[4,5-f]isoquinolin-7-one | 2-chloro-6-fluorophenyl | 2-fluoroquinolin-3-yl | 510 |
| N-{3-[2-(2-chloro-6-fluorophenyl)-7-oxo-6,7-dihydro-3H-benzo[h]imidazo[4,5-f]isoquinolin-9-yl]phenyl}acetamide | 2-chloro-6-fluorophenyl | 3-acetamidophenyl | 497 |
| N-{3-[2-(2-chloro-6-fluorophenyl)-7-oxo-6,7-dihydro-3H-benzo[h]imidazo[4,5-f]isoquinolin-9-yl]phenyl}methanesulfonamide | 2-chloro-6-fluorophenyl | 3-(methanesulfonamido)phenyl | 533 |
| N-{4-[2-(2-chloro-6-fluorophenyl)-7-oxo-6,7-dihydro-3H-benzo[h]imidazo[4,5-f]isoquinolin-9-yl]phenyl}methanesulfonamide | 2-chloro-6-fluorophenyl | 4-(methanesulfonamido)phenyl | 533 |
| 3-[2-(2-chloro-6-fluorophenyl)-7-oxo-6,7-dihydro-3H-benzo[h]imidazo[4,5-f]isoquinolin-9-yl]benzamide | 2-chloro-6-fluorophenyl | 3-carbamoylphenyl | 483 |
| 4-[2-(2-chloro-6-fluorophenyl)-7-oxo-6,7-dihydro-3H-benzo[h]imidazo[4,5-f]isoquinolin-9-yl]benzamide | 2-chloro-6-fluorophenyl | 4-carbamoylphenyl | 483 |
| 2-(2,6-difluorophenyl)-9-(1-methyl-1H-pyrazol-4-yl)-3,6-dihydro-7H-benzo[h]imidazo[4,5-f]isoquinolin-7-one | 2,6-difluorophenyl | 1-methyl-1H-pyrazol-4-yl | 428 |
| 2-(2,6-difluorophenyl)-9-(6-fluoropyridin-3-yl)-3,6-dihydro-7H-benzo[h]imidazo[4,5-f]isoquinolin-7-one | 2,6-difluorophenyl | 6-fluoropyridin-3-yl | 443 |

-continued

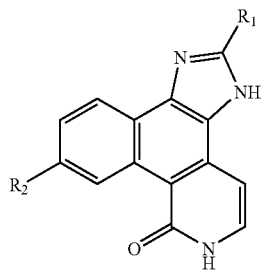

| Compound Name | R1 | R2 | M + 1 |
|---|---|---|---|
| 2-(2,6-difluorophenyl)-9-(3,4-difluorophenyl)-3,6-dihydro-7H-benzo[h]imidazo[4,5-f]isoquinolin-7-one | 2,6-difluorophenyl | 3,4-difluorophenyl | 460 |
| 4-[2-(2,6-difluorophenyl)-7-oxo-6,7-dihydro-3H-benzo[h]imidazo[4,5-f]isoquinolin-9-yl]-2-fluorobenzonitrile | 2,6-difluorophenyl | 2-fluoro-4-cyanophenyl | 467 |
| 2-(2,6-difluorophenyl)-9-(2,3,4-trifluorophenyl)-3,6-dihydro-7H-benzo[h]imidazo[4,5-f]isoquinolin-7-one | 2,6-difluorophenyl | 2,3,4-trifluorophenyl | 478 |
| 2-(2,6-difluorophenyl)-9-(2-fluoropyridin-4-yl)-3,6-dihydro-7H-benzo[h]imidazo[4,5-f]isoquinolin-7-one | 2,6-difluorophenyl | 2-fluoropyridin-4-yl | 443 |
| 2-(2,6-difluorophenyl)-9-(5-fluoropyridin-3-yl)-3,6-dihydro-7H-benzo[h]imidazo[4,5-f]isoquinolin-7-one | 2,6-difluorophenyl | 5-fluoropyridin-3-yl | 443 |
| 2-(2,6-difluorophenyl)-9-(5-fluoropyridin-2-yl)-3,6-dihydro-7H-benzo[h]imidazo[4,5-f]isoquinolin-7-one | 2,6-difluorophenyl | 5-fluoropyridin-2-yl | 443 |
| 2-(2,6-difluorophenyl)-9-(3-fluoropyridin-4-yl)-3,6-dihydro-7H-benzo[h]imidazo[4,5-f]isoquinolin-7-one | 2,6-difluorophenyl | 3-fluoropyridin-4-yl | 443 |

-continued

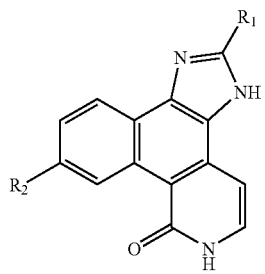

| Compound Name | R1 | R2 | M + 1 |
|---|---|---|---|
| 9-(2-chloropyridin-4-yl)-2-(2,6-difluorophenyl)-3,6-dihydro-7H-benzo[h]imidazo[4,5-f]isoquinolin-7-one | 2,6-difluorophenyl | 2-chloropyridin-4-yl | 459 |
| 2-(2,6-difluorophenyl)-9-(6-fluoropyridin-2-yl)-3,6-dihydro-7H-benzo[h]imidazo[4,5-f]isoquinolin-7-one | 2,6-difluorophenyl | 6-fluoropyridin-2-yl | 443 |
| 9-(5-chloropyridin-2-yl)-2-(2,6-difluorophenyl)-3,6-dihydro-7H-benzo[h]imidazo[4,5-f]isoquinolin-7-one | 2,6-difluorophenyl | 5-chloropyridin-2-yl | 459 |
| 2-(2,6-difluorophenyl)-9-(6-methoxypyridin-2-yl)-3,6-dihydro-7H-benzo[h]imidazo[4,5-f]isoquinolin-7-one | 2,6-difluorophenyl | 6-methoxypyridin-2-yl | 455 |
| 2-(2,6-difluorophenyl)-9-pyridin-2-yl-3,6-dihydro-7H-benzo[h]imidazo[4,5-f]isoquinolin-7-one | 2,6-difluorophenyl | pyridin-2-yl | 425 |
| 9-[4-(methylsulfonyl)phenyl]-2-(trifluoromethyl)-3,6-dihydro-7H-benzo[h]imidazo[4,5-f]isoquinolin-7-one | trifluoromethyl | 4-(methylsulfonyl)phenyl | 458 |
| 9-(1-methyl-1H-pyrazol-4-yl)-2-(trifluoromethyl)-3,6-dihydro-7H-benzo[h]imidazo[4,5-f]isoquinolin-7-one | trifluoromethyl | 1-methyl-1H-pyrazol-4-yl | 384 |
| 9-{4-[(4-methylpiperazin-1-yl)carbonyl]phenyl}-2-(trifluoromethyl)-3,6-dihydro-7H-benzo[h]imidazo[4,5-f]isoquinolin-7-one | trifluoromethyl | 4-[(4-methylpiperazin-1-yl)carbonyl]phenyl | 506 |

-continued

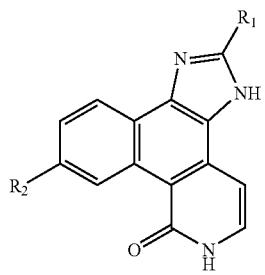

| Compound Name | R1 | R2 | M + 1 |
|---|---|---|---|
| 9-[2-(4-methylpiperazin-1-yl)pyridin-4-yl]-2-(trifluoromethyl)-3,6-dihydro-7H-benzo[h]imidazo[4,5-f]isoquinolin-7-one | CF3 | 4-methyl-2-(4-methylpiperazin-1-yl)pyridin-... | 479 |

Pharmaceutical Composition

As a specific embodiment of this invention, 100 mg of 9-bromo-2-(2-chlorophenyl)-3,6-dihydro-7H-benzo[h]imidazo[4,5-f]isoquinolin-7-one, is formulated with sufficient finely divided lactose to provide a total amount of 580 to 590 mg to fill a size 0, hard-gelatin capsule.

Biological Assays

JAK2 Kinase Activity Inhibition Assay and Determination of $IC_{50}$

The kinase activity was measured using a modified version of the homogeneous time-resolved tyrosine kinase assay described in Park et al. *Anal. Biochem.* 269, 94-104 (1999).

The procedure for determining the potency of a compound to inhibit JAK2 kinase comprises the following steps:

1. prepare 3-fold serial diluted compound/inhibitor solutions in 100% (DMSO) at 20× of the final desired concentrations in a 96 well plate;
2. prepare a master reaction mix containing 6.67 mM MgCh, 133.3 mM NaCl, 66.7 mM Tris-HCl (pH 7.4), 0.13 mg/ml BSA, 2.67 mM dithiothreitol, 0.27 recombinant JAK2 and 666.7 nM biotinylated synthetic peptide substrate (biotin-ahx-EQEDEPEGDYFEWLE-$CONH_2$) (SEQ. ID.: 1);
3. in a black assay plate, add 2.5 µl compound/inhibitor (or DMSO) and 37.5 µl master reaction mix per well; initiate the kinase reaction by adding 10 µl of 75 µM MgATP per well, allow the reactions to proceed for 80 minutes at room temperate; (the final conditions for the reactions are: 50 nM JAK2 JH1 domain (Upstate), 2.0 µM substrate, 15 µM MgATP, 5 mM $MgCl_2$, 100 mM NaCl, 2 mM DTT, 0.1 mg/ml BSA, 50 mM Tris (pH 7.4) and 5% DMSO);
4. stop the kinase reaction with 50 µl of Stop/Detection buffer containing 10 mM EDTA, 25 mM HEPES, 0.1% TRITON X-100, 0.126 µg/ml Eu-chelate labeled anti-phosphotyrosine antibody PY20 (cat. # AD0067, PerkinElmer) and 45 µg/ml Streptavidm-allophycocyanin conjugate (cat. #PJ25S, Prozyme); and
5. read HTRF signals on a Victor reader (PerkinElmer) in HTRF mode after 60 minutes.

$IC_{50}$ was obtained by fitting the observed relationship between compound/inhibitor concentration and HTRF signal with a 4-parameter logistic equation.

Compounds of the instant invention are potent inhibitors of recombinant purified JAK2 kinase activity with an $IC_{50}$ of approximately 0.1 nM-20 µM.

JAK1 Enzyme Assay

For the JAK1 enzyme assay, reactions (50 uL) contained 5× IVGN buffer (50 mM Hepes, pH 7.5, 10 mM MgCl2, 0.01% Brij-35, 1 mM EGTA, 0.1 mg/ml BSA), 2 mM DTT, 2.0 µM peptide substrate, 25 µM MgATP, 400 pM JAK1 enzyme and subject compound in 5% DMSO. Reactions were incubated for 60 min at RT and quenched with 50 µL 2× quench detect buffer (10 mM EDTA, 25 mM HEPES, 0.1% TRITON X-100, 4.7 uM Europium-Py20 and 2.1 mg/mL streptavidin-APC). Incubate 1 hr at RT and read on a Victor V3 set to read Fluorescent Resonance Energy Transfer (Label 1: Lance 615, Label 2: Lance 665, For both: delay=50 us, window time=100 us, cycle=1000 us, flash energy level=103)

Peptide substrate is amino hexanoyl biotin-EQEDEPEGDYFEWLE-NH2 (SEQ. ID.: 1); in DMSO.

TYK2 Enzyme Assay

For the TYK2 enzyme assay, reactions (50 uL) contained 5× IVGN buffer (50 mM Hepes, pH 7.5, 10 mM MgCl2, 0.01% Brij-35, 1 mM EGTA, 0.1 mg/ml BSA), 2 mM DTT, 2.0 µM peptide substrate, 15 µM MgATP, 125 pM enzyme and subject compound in 5% DMSO. Reactions were incubated for 60 min at RT and quenched with 50 uL 2× quench detect buffer (10 mM EDTA, 25 mM HEPES, 0.1% TRITON X-100, 4.7 uM Europium-Py20 and 2.1 mg/mL streptavidin-APC). Incubate 1 hr at RT and read on a Victor V3 set to read Fluorescent Resonance Energy Transfer (Label 1: Lance 615, Label 2: Lance 665, For both: delay=50 us, window time=100 us, cycle=1000 us, flash energy level=103)

Peptide substrate is amino hexanoyl biotin-EQEDEPEGDY-FEWLE-NH2 (SEQ. ID.: 1);in DMSO.

Assay For JAK Family Protein Kinase Activity

Materials. Streptavidin•allophycocyanin conjugate (SA•APC) and Europium•cryptate (Eu•K) were from Packard Instrument Company. Eu•K conjugated pY20 was produced as described in Cummings, R. T.; McGovern, H. M.; Zheng, S.; Park, Y. W. and Hermes, J. D. Use Of A Phosphotyrosine-Antibody Pair As A General Detection Method In Homogeneous Time Resolved Fluorescence-Application To Human Immunodeficiency Viral Protease. *Analytical Biochemistry* 1999, 33, 79-93. Homogenous time resolved fluorescence (HTRF) measurements were made using the Discovery instrument from Packard. T-stim Culture Supplement was from Collaborative Biomedical Research. Recombinant mouse IL2 was from Pharmingen or R & D.

JAK family kinase expression. JAK3, TYK2 and JAK2 kinase domains with N-terminal "Flag" affinity tags were expressed in Sf9 cells using standard baculovirus methods. The human JAK3 gene was provided by Dr. John J. O'Shea (NTH). The human TYK2 gene was provided by Dr. Sandra Pellegrini (Insitut Pasteur). Human JAK2 kinase domain was cloned from a MOLT4cDNA library (Clonetech).

Assay for JAK family protein kinase activity. Tyrosine kinase activity was measured by detection of the tyrosine phosphorylated peptide amino hexanoyl biotin-EQEDE-PEGDYFEWLE-NH$_2$ (SEQ. ID.: 1); (S, hereafter) detected by time-resolved fluorescence using a europium labeled antibody to phosphotyrosine (pY20). The JAK3 (JH1) catalyzed phosphorylation reactions were carried out in a 30 uL total reaction volume. The compound was run at 5% DMSO and preincubated with enzyme buffer (EB). The EB comprised Invitrogen 5× kinase buffer (50 mM Hepes, pH 7.5, 10 mM MgCl2, 0.01% Brij-35, 1 mM EGTA, 0.1 mg/ml BSA), 2 mM (final) DTT, 2 µM (final) S, and 250 pM (final) JAK3 enzyme. The assay was run at ATP K$_m$ (5 µM final) for 40 to 80 minutes. Reactions were run at ambient temperature and quenched with an equal volume of quench buffer (QB) (10 mM EDTA, 25 mM HEPES, 0.1% TRITON X-100) containing 50 µg/mL SA•APC conjugate and 0.75 nM Eu•K conjugated pY20. This mixture was incubated at ambient temperature for at least 60 minutes and read on an optimized fluorescent reader at Ex=320nm and Em$_1$=665 nm (SA−APC) and Em$_2$=615 nM (Eu). The data was analyzed by using a standard 4P fit on the ratio of the Em results: (EM$_1$÷EM$_2$) *10,000.

Cellular proliferation assays. CTLL-2 cells (ATCC) were maintained in 6% T-stim Culture Supplement (source of IL2) in RPMI-1640 supplemented with 10% fetal bovine serum, 1 mM sodium pyruvate, 50 µM β-mercaptoethanol, 1.4 mM L-glutamine, 10 mM HEPES, 1 mg/ml dextrose, 0.04 mM essential amino acids, 0.02 mM nonessential amino acids, penicillin and streptomycin (H10). The day before use in the proliferation assay, cells were washed and resuspended in 0.2% Tstim at a cell concentration of $5 \times 10^5$/ml. The next day, cells were washed and plated at $0.2$-$1 \times 10^5$ cells/well in a 96 well tissue culture plate (CoStar). 0.05 ng/ml mouse recombinant IL2 (Pharmingen), with or without a test compound, or 20 ng/ml PMA (Sigma) and 1 µCi/well [$^3$H]-thymidine were added. After overnight culture, cells were harvested with a glass fiber Filtermat (Wallac) and a Tomtek cell harvester. Tritium incorporation was measured by liquid scintillation counting on a Topcount scintillation counter (Packard).

Compounds of the instant invention are potent inhibitors of recombinant purified JAK3 kinase activity with an IC$_{50}$ of approximately 0.1 nM-20 µM.

In vitro PDK1 Kinase Assay

Activated recombinant full-length mT(Glu-Glu-Phe) tagged human PDK1 is used to determine whether the compounds of the instant invention modulate the enzymatic activity of this kinase.

The cDNA, encoding full-length PDK1, is subcloned into a baculovirus expression vector pBlueBac4.5 (Invitrogen), containing an in frame middle T tag (MEYMPME) at its N-terminus. Soluble activated recombinant full-length mT(Glu-Glu-Phe) tagged human PDK1 is expressed in a baculovirus-infected Sf9 insect cells (Kemp Biotechnologies), according to the protocol recommended by the manufacturer. Immunoaffinity purification of the PDK1 kinase from the insect cell lysate is performed using a middle Tag antibody bound to Protein G-EE column. Upon elution using 50 mM Tris pH 7.4, 1 mM EDTA, 1 mM EGTA, 0.5 mM Na$_3$VO$_4$, 1 mM DTT, 50 mM NaF, Na Pyrophospate, Na-β-glycerophosphate, 10% glycerol, Complete, 1 µM microcystein, and 50 µg/ml EYMPME peptide, fractions containing PDK1 protein are pooled together, based on SDS-PAGE and western blot analyses, and then analyzed for protein concentration using BCA Protein Assay (Pierce) with BSA as standard. The final product was aliqouted and flash frozen in liquid nitrogen before being stored at −80° C. Resulting PDK1 protein has MW of 64 kDa, is phosphorylated 'by default' and purifies as an activated kinase from insect cells.

The procedure for determining the potency of a compound to inhibit PDK1 kinase comprises the following steps:

1. Prepare 3-fold serial diluted compound solutions in 100% dimethyl sulfoxide (DMSO) at 20× of the desired final concentrations in a 384-well plate.
2. Prepare a master reaction mix containing 62.5 mM HEPES (pH 7.5), 12.5 mM MgCl$_2$, 0.013% Brij-35, 1.25 mM EGTA, 2.5 mM dithiothreitol, 1.25 nM recombinant PDK1 and 375 nM biotinylated synthetic peptide substrate (Biotin-GGDGATMKTFCGGTPSDGDP-DGGEFTEF-COOH) (SEQ. ID.: 2).
3. In a black assay plate, add 2.5 µl of compound solution (or DMSO) and 22.5 µl of master reaction mix per well. Pre-incubate for 10 min. Initiate the kinase reaction by adding 6 µl of 0.25 mM MgATP per well. Allow the reactions to proceed for 25 min at room temperature. The final conditions for the reaction are 1 nM PDK1, 300 nM peptide substrate, 5 uM MgATP, 10 mM MgCl$_2$, 2 mM DTT, 50 mM HEPES (pH 7.5), 0.01% Brij-35, 1 mM EGTA and 5% DMSO.
4. Stop the kinase reaction with 30 µl of Stop/Detection buffer containing 10 mM EDTA, 1× Lance Detection Buffer (cat. # CR97-100, PerkinElmer), 1% Super-Blocking in TBS (cat. # 37535, Pierce), 5 nM phospho-Akt(T308) monoclonal antibody (cat. # 4056, Cell Signaling Technologies), 5 nM Lance labeled Eu-Anti-rabbit IgG (cat. # AD0083, PerkinElmer), and 100 nM Streptavidin-allophycocyanin conjugate (cat. # PJ25S, Prozyme).
5. Read HTRF signals on an Envision reader (PerkinElmer) in HTRF mode after 60 min.
6. IC50 is determined by fitting the observed relationship between compound concentration and HTRF signal with a 4-parameter logistic equation.

The compounds described in the Examples were tested in the above assay and found to have an $IC_{50} \leq 50$ μM.

While a number of embodiments of this invention have been described, it is apparent that the basic examples may be altered to provide other embodiments, encompassed by the present invention. Therefore, it will be appreciated that the scope of this invention is to be defined by the appended claims rather than by the specific embodiments, which have been represented by way of example.

What is claimed is:

1. A compound of the formula

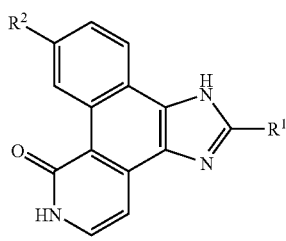

wherein $R^1$ is aryl, wherein said aryl, groups is optionally substituted with one to three substituents independently selected from the group consisting of halo, hydroxyl, $C_{1-6}$alkyl, $O(C_{1-6}$alkyl), $R^3$ and halolakyl;

$R^2$ is heteroaryl, wherein said heteroaryl, group is optionally substituted with one to three substituents independently selected from the group consisting of $R^3$, hydroxyl, cyano, halo, $C_{1-6}$alkyl, $O(C_{1-6}$alkyl), $O(C_{1-6}$alkyl)$R^3$, $(C_{1-6}$alkyl)$R^3$, $(C\!=\!O)R^3$, $OR^3$, $(C\!=\!O)R^3OH$, $(C\!=\!O)R^3O(C_{1-6}$alkyl), $(C\!=\!O)O(C_{1-6}$alkyl), $R^3(C\!=\!O)O(C_{1-6}$alkyl), $SO_mR^3$, $SO_mR^4$, $(C\!=\!O)NR^4R^5$, $(C\!=\!O)NR^4(C_{1-6}$alkyl)$R^3$; $(C\!=\!O)NR^4(C_{1-6}$alkyl)$NR^4R^5$, $(C\!=\!O)O(C_{1-6}$alkyl), $(C\!=\!O)NR^4SO_m(C_{1-6}$alkyl), $NR^4R^5$, $(C\!=\!O)NR^4R^5$, $N(R^3)_2$, $NR^4(C_{1-6}$alkyl)$R^3$, $NR^4(C\!=\!O)C_{1-6}$alkyl, $NR^4SO_m(C_{1-6}$alkyl), $(C_{1-6}$alkyl)$NR^4R^5$ and $NHSO_m N(R^3)_2$;

each $R^3$ is independently aryl, heteroaryl, heterocyclyl or $C_{3-8}$cycloalkyl, wherein said aryl, heteroaryl, heterocyclyl and cycloalkyl groups are optionally substituted with one to three halo, hydroxyl or $C_{1-6}$alkyl;

$R^4$ is hydrogen or $C_{1-6}$alkyl;

$R^5$ is hydrogen or $C_{1-6}$alkyl;

m is an integer from zero to two;

or a pharmaceutically acceptable salt or stereoisomer thereof.

2. The compound of claim 1 wherein $R^1$ is phenyl substituted with two halo; or a pharmaceutically acceptable salt or stereoisomer thereof.

3. The compound of claim 1 wherein $R^2$ is heteroaryl, wherein said heteroaryl group is optionally substituted with one to three substituents independently selected from the group consisting of $R^3$, hydroxyl, cyano or halo; or a pharmaceutically acceptable salt or stereoisomer thereof.

4. The compound of claim 3 wherein $R^2$ is heteroaryl, wherein said heteroaryl group is optionally substituted with one to three substituents independently selected from the group consisting of hydroxyl, cyano and halo; or a pharmaceutically acceptable salt or stereoisomer thereof.

5. The compound of claim 3 wherein $R^2$ is heteroaryl wherein said heteroaryl group is optionally substituted with one to two substituents independently selected from the group consisting of hydroxyl, cyano and halo; or a pharmaceutically acceptable salt or stereoisomer thereof.

6. The compound which is:

2-cyclopentyl-9-(1-methyl-1H-pyrazol-4-yl)-3,6-dihydro-7H-benzo[h]imidazo[4,5-f]isoquinolin-7-one;
2-(2-chloro-6-fluoropheny)-9-(6-chloropyridin-3-yl)-3,6-dihydro-7H-benzo [h]imidazo[4,5-f]isoquinolin-7-one;
9-(5-chloropyridin-2-yl)-2-(2,6-difluorophenyl)-3,6-dihydro-7H-benzo[h]imidazo[4,5-f]isoquinolin-7-one;
2-(2-chloro-6-fluorophenyl)-9-(2,6-difluoropyridin-3-yl)-3,6-dihydro-7H-benzo [h]imidazo[4,5-f]isoquinolin-7-one;
2-(2-chlorophenyl)-9-(1-methyl-1H-pyrazol-4-yl)-3,6-dihydro-7H-benzo[h]imidazo[4,5-f]isoquinolin-7-one;
2-(2-chlorophenyl)-9-pyridin-4-yl-3,6-dihydro-7H-benzo[h]imidazo[4,5-f]isoquinolin-7-one;
2-(2-chlorophenyl)-9-pyridin-3-yl-3,6-dihydro-7H-benzo[h]imidazo[4,5-f]isoquinolin-7-one;
2-(2-chlorophenyl)-9-[2(4-methylpiperazin-1-yl)pyridine-4-yl]-3,6-dihydro-7H-benzo [h]imidazo[4,5-f]isoquinolin-7-one;
2-(2-chlorophenyl)-9-(1H-pyrazol-3-yl)-3,6-dihydro-7H-benzo[h]imidazo[4,5-f]isoquinolin-7-one;
2-(2-chlorophenyl)-9-[4-methylpiperazin-1-yl)pyridin-3-yl]-3,6-dihydro-7H-benzo [h]imidazo[4,5-f]isoquinolin-7-one;
2-cyclopentyl-9-(1H-pyrazol-3-yl)-3,6-dihydro-7H-benzo[h]imidazo[4,5-f]isoquinolin-7-one;
9-(1H-pyrazol-3-yl)-2-(tetrahydrofuran-3-yl)-3,6-dihydro-7H-benzo[h]imidazo[4,5-f]isoquinolin-7-one;
9-(1H-pyrazol-3-yl)-2-(tetrahydrofuran-3 -yl)-3,6-dihydro-7H-benzo[h]imidazo[4,5-f]isoquinolin-7-one;
2-cyclopentyl-9-(6-methoxypyridin-3-yl)-3,6-dihydro-7H-benzo[h]imidazo[4,5-f]isoquinolin-7-one;
2-cyclopentyl-9-(1H-pyrazol-4-yl)-3,6-dihydro-7H-benzo[h]imidazo[4,5-f]isoquinolin-7-one;
2-cyclopentyl-9-(2,6-dimethoxypyridin-3-yl)-3,6-dihydro-7H-benzo[h]imidazo[4,5-f]isoquinolin-7-one;
2-cyclopentyl-9-pyrimidin-5-yl-3,6-dihydro-7H-benzo[h]imidazo[4,5-f]isoquinolin-7-one;
2-cyclopentyl-9-(3,5-dimethylisoxazol-4-yl)-3,6-dihydro-7H-benzo[h]imidazo[4,5-f]isoquinolin-7-one;
2-(2-chloro-6-fluorophenyl)-9-(1H-pyrazol-3-yl)-1,6-dihydro-7H-benzo[h]imidazo[4,5-f]isoquinolin-7-one;
2-(2-chloro-6-fluorophenyl)-9-(1H-pyrazol-4-yl)-3,6-dihydro-7H-benzo[h]imidazo[4,5-f]isoquinolin-7-one;
2-(2-chloro-6-fluorophenyl)-9-pyridin-3-yl-1,6-dihydro-7H-benzo[h]imidazo[4,5-f]isoquinolin-7-one;
2-(2-chloro-6-fluorophenyl)-9-(2-morpholin-4-ylpyridin-4-yl)-3,6-dihydro-7H-benzo[h]imidazo[4,5-f]isoquinolin-7-one;
2-(2-chloro-6-fluorophenyl)-9-pyridin-4-yl-3,6-dihydro-7H-benzo[h]imidazo[4,5-f]isoquinolin-7-one;
9-(6-aminopyridin-3-yl)-2-(2-chloro-6-fluorophenyl)-3,6-dihydro-7H-benzo [h]imidazo[4,5-f]isoquinolin-7-one;
2-(2-chloro-6-fluorophenyl)-9-(6-methoxypyridin-3-yl)-3,6-dihydro-7H-benzo[h]imidazo[4,5-f]isoquinolin-7-one;
2-(2-chloro-6-fluorophenyl)-9-(4-methoxypyridin-3-yl)-3,6-dihydro-7H-benzo[h]imidazo[4,5-f]isoquinolin-7-one;
2-(2-chloro-6-fluorophenyl)-9-{6-[(2-morpholin-4-ylethyl)amino]pyridin-3-yl}-3,6-dihydro-7H-benzo[h]imidazo[4,5-f]isoquinolin-7-one;
2-(2-chloro-6-fluorophenyl)-9-(6-hydroxypyridin-3-yl)-3,6-dihydro-7H-benzo[h]imidazo[4,5-f]isoquinolin-7-one;
2-(2-chloro-6-fluorophenyl)-9-(5-chloro-2-methoxypyridin-4-yl)-3,6-dihydro-7H-benzo [h]imidazo[4,5-f]isoquinolin-7-one;
2-(2-chloro-6-fluorophenyl)-9-(6-chloropyridin-3-yl)-3,6-dihydro-7H-benzo[h]imidazo[4,5-f]isoquinolin-7-one;
2-(2-chloro-6-fluorophenyl)-9-[2-(cyclopropylmethoxy)pyridin-3-yl]-3,6-dihydro-7H-benzo[h]imidazo[4,5-f]isoquinolin-7-one; p1 2-(2-chloro-6-fluorophenyl)-9-(6-fluoropyridin-3-yl)-3,6-dihydro-7H-benzo [h]imidazo[4,5-f]isoquinolin-7-one;
5-[2-(2-chloro-6-fluorophenyl)-7-oxo-6,7-dihydro-3H-benzo[h]imidazo[4,5-f ]isoquinolin-9-yl]pyridine-2-carbonitrile;
2-(2-chloro-6-fluorophenyl)-9-(2,6-difluoropyridin-3-yl)-3,6-dihydro-7H-benzo [h]imidazo[4,5-f]isoquinolin-7-one;
2-(2-chloro-6-fluorophenyl)-9-(6-methylpyridin-3-yl)-3,6-dihydro-7H-benzo [h]imidazo[4,5-f]isoquinolin-7-one;
2-(2-chloro-6-fluorophenyl)-9-pyrimidin-5-yl-3,6-dihydro-7H-benzo[h]imidazo[4,5-f ]isoquinolin-7-one;
2-(2-chloro-6-fluorophenyl)-9-quinolin-3-yl-3,6-dihydro-7H-benzo[h]imidazo[4,5-f ]isoquinolin-7-one;
2-(2-chloro-6-fluorophenyl)-9-[6-(dimethylamino)pyridin-3-y]-3,6-dihydro-7H-benzo [h]imidazo[4,5-f]isoquinolin-7-one;
2-(2-chloro-6-fluorophenyl)-9-(3-furyl)-3,6-dihydro-7H-benzo[h]imidazo[4,5-f ]isoquinolin-7-one;
2-(2-chloro-6-fluorophenyl)-9-(1-methyl-1H-pyrazol-4-yl)-3,6-dihydro-7H-benzo [h]imidazo[4,5-f]isoquinolin-7-one;
2-(2-chloro-6-fluorophenyl)-9-(2,6-dimethoxypyridin-3yl)-3,6-dihydro-7H-benzo [h]imidazo[4,5-f]isoquinolin-7-one;
2-(2-chloro-6-fluorophenyl)-9-(3,5-dimethyl-1H-pyrazol-4-yl)-3,6-dihydro-7H-benzo [h]imidazo[4,5-f]isoquinolin-7-one;
2-(2-chloro-6-fluorophenyl)-9-(1,3,5-trimethyl-1H-pyrazol-4-yl)-3,6-dihydro-7H-benzo [h]imidazo[4,5-f]isoquinolin-7-one;
2-(2-chloro-6-fluorophenyl)-9-isoquinolin-4-yl-3,6-dihydro-7H-benzo[h]imidazo[4,5-f ]isoquinolin-7-one;
2-(2-chloro-6-fluorophenyl)-9-(2-methoxypyrimidin-5-yl)-3,6-dihydro-7H-benzo[h]imidazo[4,5-f]isoquinolin-7-one;
2-(2-chloro-6-fluorophenyl)-9-(6-morpholin-4-ylpyridin-3-yl)-3,6-dihydro-7H-benzo [h]imidazo[4,5-f]isoquinolin-7-one;
2-(2-chloro-6-fluorophenyl)-9-(2-methoxypyridin-3-yl)-3,6-dihydro-7H-benzo [h]imidazo[4,5-f]isoquinolin-7-one;
2-(2-chloro-6-fluorophenyl)-9-(2-fluoroquinolin-3-yl)-3,6-dihydro-7H-benzo [h]imidazo[4,5-f]isoquinolin-7-one;
2-(2,6-difluorophenyl)-9-(1-methyl-1H-pyrazol-4-yl)-3,6-dihydro-7H-benzo [h]imidazo[4,5-f]isoquinolin-7-one;
2-(2,6-difluorophenyl)-9-(6-fluoropyridin-3-yl)-3,6-dihydro-7H-benzo[h]imidazo[4,5-f]isoquinolin-7-one;
2-(2,6-difluorophenyl)-9-(2-fluoropyridin-4-yl)-3,6-dihydro-7H-benzo[h]imidazo[4,5-f]isoquinolin-7-one;
2-(2,6-difluorophenyl)-9-(5-fluoropyridin-3-yl)-3,6-dihydro-7H-benzo[h]imidazo[4,5-f]isoquinolin-7-one;

2-(2,6-difluorophenyl)-9-(5-fluoropyridin-2-yl)-3,6-dihydro-7H-benzo[h]imidazo[4,5-f]isoquinolin-7-one;
2-(2,6-difluorophenyl)-9-(3-fluoropyridin-4-yl)-3,6-dihydro-7H-benzo[h]imidazo[4,5-f]isoquinolin-7-one;
9-(2-chloropyridin-4-yl)-2-(2,6-difluorophenyl)-3,6-dihydro-7H-benzo[h]imidazo[4,5-f]isoquinolin-7-one;
2-(2,6-difluorophenyl)-9-(6-fluoropyridin-2-yl)-3,6-dihydro-7H-benzo[h]imidazo[4,5-f]isoquinolin-7-one;
9-(5-chloropyridin-2-yl)-2-(2,6-difluorophenyl)-3,6-dihydro-7H-benzo[h]imidazo[4,5-f]isoquinolin-7-one;
2-(2,6-difluorophenyl)-9-(6-methoxypyridin-2-yl)-3,6-dihydro-7H-benzo[h]imidazo[4,5-f]isoquinolin-7-one;
2-(2,6-difluorophenyl)-9-pyridin-2-yl-3,6-dihydro-7H-benzo[h]imidazo[4,5-f]isoquinolin-7-one;
or a pharmaceutically acceptable salt or stereoisomer thereof.

7. A pharmaceutical composition comprising a pharmaceutically effective amount of the compound according to claims 1, and a pharmaceutically acceptable carrier.

* * * * *